(12) United States Patent
Krieg et al.

(10) Patent No.: US 9,591,856 B2
(45) Date of Patent: Mar. 14, 2017

(54) FUNGICIDE COMPOSITIONS COMPRISING FLUOPYRAM, AT LEAST ONE SUCCINATE DEHYDROGENASE (SDH) INHIBITOR AND OPTIONALLY AT LEAST ONE TRIAZOLE FUNGICIDE

(71) Applicant: BAYER INTELLECTUAL PROPERTY GMBH, Monheim (DE)

(72) Inventors: Ulrich Krieg, Leverkusen (DE); Damien Viollet, Düsseldorf (DE); Andreas Görtz, Dormagen (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 89 days.

(21) Appl. No.: 14/370,655

(22) PCT Filed: Jan. 8, 2013

(86) PCT No.: PCT/EP2013/050195
§ 371 (c)(1),
(2) Date: Jul. 3, 2014

(87) PCT Pub. No.: WO2013/104609
PCT Pub. Date: Jul. 18, 2013

(65) Prior Publication Data
US 2014/0378514 A1   Dec. 25, 2014

(30) Foreign Application Priority Data

Jan. 9, 2012   (EP) ..................... 12150455

(51) Int. Cl.
*A61K 31/44* (2006.01)
*A01N 43/40* (2006.01)
*A01N 43/56* (2006.01)
*A01N 43/653* (2006.01)

(52) U.S. Cl.
CPC ............ *A01N 43/40* (2013.01); *A01N 43/56* (2013.01); *A01N 43/653* (2013.01)

(58) Field of Classification Search
CPC .. A01N 43/56; A01N 43/653; A01N 2300/00; A01N 43/40
USPC ........................................................ 514/357
See application file for complete search history.

(56) References Cited

U.S. PATENT DOCUMENTS

| 8,486,858 B2 * | 7/2013 | Seitz .................. A01N 43/653 504/100 |
| 2007/0060579 A1 | 3/2007 | Wachendorff-Neumann et al. |
| 2007/0123541 A1 | 5/2007 | Grosjean-Cournoyer et al. |
| 2012/0088662 A1 | 4/2012 | Dietz et al. |
| 2012/0088665 A1 * | 4/2012 | Dietz .................. A01N 37/50 504/100 |
| 2014/0100107 A1 * | 4/2014 | Wachendorff-Neumann A01N 43/653 504/100 |
| 2014/0113899 A1 * | 4/2014 | Tateishi ............. A01N 43/653 514/239.5 |
| 2014/0256716 A1 * | 9/2014 | Baur .................. A01N 25/02 514/229.2 |

FOREIGN PATENT DOCUMENTS

| AU | WO 2011128262 A2 * | 10/2011 | ............. A01N 37/50 |
| EP | 1751109 B1 | 4/2009 | |
| JP | WO 2012169523 A1 * | 12/2012 | ........... A01N 43/653 |
| WO | 2005077901 A1 | 8/2005 | |
| WO | 2010146006 A2 | 12/2010 | |
| WO | 2011110583 A2 | 3/2011 | |
| WO | 2012072660 A1 | 11/2011 | |

OTHER PUBLICATIONS

International Search Report received in PCT/EP2013/050195, mailed Mar. 12, 2013.
M. Tsimilli-Michael, et al., Synergistic and antagonistic effects of arbuscular mycorrhizal fungi and Azospirillum and Rhizobium nitrogen-fixers on the photosynthetic activity of alfalfa, probed by the polyphasic chlorophyll a fluorescence transient O-J-I-Pq, Applied Soil Ecology, 2000, pp. 169-182.
H. F. Avenot, et al., Molecular characterization of boscalid and penthiopyrad-resistant isolates of Didymella bryoniae and assessment of their sensitivity to fluopyram, 2011 Society of Chemical Industry, Pest Manag Sci 2012, pp. 645-651.
H. F. Avenot, et al., Progress in understanding molecular mechanisms and evolution of resistance to succinate dehydrogenase inhibiting (SDHI) fungicides in phytopathogenicfungi, Crop Protection 29 (2010), pp. 643-651.
M. Hruskova et al., Prediction of Wheat and Flour Zeleny Sedimentation Value Using NIR Technique, Czech J. Food Sci., vol. 21, No. 3, pp. 91-96.
P.M.L. Tammes, Isoboles, A Graphic Representation of Synergism in Pesticides, Neth. J. Plant Path. 70 (1964), pp. 73-80.
S.R. Colby, Calculating Synergistic and Antagonistic Responses of Herbicide Combinations, pp. 20-22, (1967).

* cited by examiner

*Primary Examiner* — My-Chau T Tran
(74) *Attorney, Agent, or Firm* — McBee Moore Woodward Vanik IP LLC

(57) ABSTRACT

The present invention relates to novel fungicide compositions comprising (A) fluopyram, (B) at least one further succinate dehydrogenase (SDH) inhibitor and optionally further (C) at least one triazole fungicide, whereas the invention especially comprises such novel fungicide compositions of (A) fluopyram, (B) bixafen and (C) at least one triazole fungicide, which is preferably prothioconazole. The present invention also relates to the use of such novel fungicide compositions for improving growth in crops, comprising preventively and/or curatively controlling pathogenic fungi and/or nematodes, resistance management, and improving plant physiology effects by enhancing root growth, improving greening, improving water use efficiency, improving nitrogen-use efficacy, delaying senescence and enhancing yield.

19 Claims, No Drawings

FUNGICIDE COMPOSITIONS COMPRISING FLUOPYRAM, AT LEAST ONE SUCCINATE DEHYDROGENASE (SDH) INHIBITOR AND OPTIONALLY AT LEAST ONE TRIAZOLE FUNGICIDE

CROSS REFERENCE TO RELATED APPLICATIONS

This application is a §371 National Stage Application of PCT/EP2013/050195, filed Jan. 8, 2013, which claims priority to EP 12150455.9, filed Jan. 9, 2012.

BACKGROUND

Field of the Invention

The present invention relates to novel fungicide compositions comprising (A) fluopyram, (B) at least one further succinate dehydrogenase (SDH) inhibitor and optionally further (C) at least one triazole fungicide, whereas the invention especially comprises such novel fungicide compositions of (A) fluopyram, (B) bixafen and (C) at least one triazole fungicide, which is preferably prothioconazole. The present invention also relates to the use of such novel fungicide compositions for improving growth in crops, comprising preventively and/or curatively controlling pathogenic fungi and/or nematodes, resistance management and improving plant physiology effects by enhancing root growth, improving greening, improving water use efficiency, improving nitrogen-use efficacy, delaying senescence and enhancing yield.

Description of Related Art:

International patent application WO 2005/077901 A1 and the corresponding European patent EP 1751109 B1 generally disclose fungicide compositions comprising a pyridylethylbenzamide derivative and a compound capable of inhibiting the transport of electrons of the respiratory chain in phytopathogenic fungal organisms. Object of this earlier invention are mainly binary compositions referring inter alia to the binary combination of fluopyram and bixafen. Further it is generally stated therein, that such binary compositions may further comprise additional fungicides but no concrete ternary combinations are specified. Thus the specific ternary combination of fluopyram, bixafen and a fungicide which is selected from the group of triazole fungicides or even more the concrete ternary combination of fluopyram, bixafen and prothioconazole is new in the sense of a selection invention as on the one hand the binary combination of (A) fluopyram and (B) bixafen is selected from a first list of possible binary combinations and the triazole fungicide, especially prothioconazole (C) is selected from a second general list of fungicides.

Furthermore the inventors of the present invention surprisingly found the new use of a binary combination of (A) fluopyram and (B) a succinate dehydrogenase (SDH) inhibitor, which may optionally further comprise (C) at least one triazole fungicide for improving growth in crops, wherein the improvement is characterized by at least one of the effects of the group consisting of preventively and/or curatively controlling pathogenic fungi and/or nematodes, resistance management and improving plant physiology effects by enhancing root growth, improving greening, improving water use efficiency, improving nitrogen-use efficacy, delaying senescence and enhancing yield.

Especially the use of such fungicidal composition combinations for preventively and/or curatively controlling pathogenic fungi, comprising resistance management, in cereals and/or relating to selected pathogenic fungi is a selection invention over WO 2005/077901 A1 and the corresponding EP 1751109 B1 as therein combinations of fluopyram and SDH inhibitors (complex II inhibitors) specifically only refer to the treatment of *Cucumis sativus* species crops and the treatment of *Botrytis* sp. or *Sphaerotheca fuliginea*.

Thus the selection of the combination of fluopyram with a complex II inhibitor (SDH inhibitor) on the one hand and the selection of the treatment of cereals and cereal destruents, respectively, on the other hand can be seen as a selection invention over the mentioned prior art. Even more, the selection of on the one hand the even more specific ternary active compound combination of (A) fluopyram and (B) a SDH inhibitor and (C) a triazole fungicide is selected from a first list of possible active compound combinations and on the other hand the specific use for preventively and/or curatively controlling pathogenic fungi, comprising resistance management, in cereals and/or for selected pathogenic fungi is selected from a second list of possible effects or uses.

The same holds true for the international patent application WO 2012/072660 A1, which relates to the use of fluopyram for controlling nematodes in crops. This document further generally mentions the use of fluopyram in combination with additional agrochemically active compounds as combination partners, which may be selected from the group consisting of fungicides, bactericides, insecticides, acaricides, nematicides, molluscicides, safeners, plant growth regulators and plant nutrients as well as biological control agents. The diverse lists of such potential combination partners inter alia comprise a list of SDH inhibitors, the list comprising inter alia bixafen, and a list of fungicides, comprising inter alia triazole fungicides as e.g. prothioconazole.

Nevertheless, no concrete combination of fluopyram with an active ingredient from the group of SDH inhibitors and further with a triazole fungicide or even more the concrete combination of fluopyram with bixafen and optionally prothioconazole for the use in the treatment of crops against nematodes is disclosed therein. Even more, the concrete examples solely refer to the use of fluopyram alone but not to any binary or ternary active ingredient composition. Accordingly, the use of the active ingredient combination of the present invention in the treatment of crops for preventively and/or curatively controlling nematodes is new, too.

The international patent application WO 2011/110583 A2 describes fungicidal combinations and compositions, useful e.g. for controlling phytopathogenic fungi, comprising a triazolyl compound of formula (I) and at least one fungicidal compound selected from a large group of fungicides. Most of triazole fungicides claimed as combination partners in the present invention are not covered by Formula (I) of WO 2011/110583 A2, including the most preferred triazole fungicides prothioconazole, tebuconazole, and epoxyconazole. There are also ternary combinations listed in extensive tables, some of them comprising fluopyram and bixafen, however, the third combination partner, a triazole, is different from the triazole fungicides claimed in the present invention.

The international patent application WO 2010/146006 A2 relates to fungicidal composition comprising an azolylmethyloxirane compound of formula (I) and a second component selected from a large group of fungicides and other agrochemical compounds. None of the triazole fungicides claimed as combination partners in the present invention are covered by Formula (I) of WO 2010/146006 A2. There are also ternary combinations listed in extensive tables, some of them comprising fluopyram and bixafen, however, the third combination partner, an azolylmethyloxirane, is different from the triazole fungicides claimed in the present invention. Further, there are quaternary combinations listed in extensive tables comprising fluopyram, bixafen and prothioconazole, in addition to an azolylmethyloxirane of formula (I) that is not claimed in the present invention.

The US patent application US 2007/123541 relates fungicidal compositions comprising at least a pyridylethylbenzamide derivative of formula (I) and a compound capable of inhibiting the ergosterol biosynthesis, e.g. a triazole, imidazole, morpholine, or piperidine derivative, fenhexamide, spiroxamine, or triforine, and optionally one further fungicide. Preferably, the pyridylethylbenzamide derivative is fluopyram. The examples show synergistic fungicidal combinations comprising fluopyram and different triazole fungicides on infected wheat plants. There are ternary combinations claimed but bixafen is not disclosed as additional combination partner.

The US patent application US 2007/060579 relates to binary fungicidal combinations comprising bixafen (1-1) and a further fungicide selected from a large list. This list also includes a number of triazole fungicides but it does not include fluopyram. Additionally, in any case the use of such active compound compositions for improving plant physiology effects such as e.g. for enhanced root growth, improved greening, improved water use efficiency, improved nitrogen-use efficacy, delayed senescence and enhanced yield, either alone or in combination with one or more of the effects as described herein, has not been mentioned in such earlier prior art documents and is thus clearly new.

The beneficial effects and new use of the selected active ingredient compositions of the present invention have now been shown by the inventors of the present invention for the first time and were not obviously suggested by the mentioned documents.

An overview of molecular mechanisms and evolution of resistance to SDHI fungicides in phytopathogenic fungi is given in Avenot, H F et al., Crop Protection 29 (2010) 643-651. This article also describes cross-resistance relationships between the SDHI fungicides boscalid, penthiopyrad, and fluopyram. Assuming a positive cross-resistance pattern for fungicides acting in mitochondrial complex II, the sensitivity profile of selected *Alternaria alternata* boscalid-resistant mutants and wild-type isolates to penthiopyrad and fluopyram was determined. Whereas the *Alternaria alternata* boscalid-resistant isolates carrying SDH-mutations were not affected by penthiopyrad, fluopyram in vitro strongly inhibited the mycelial growth of *Alternaria alternata* SDH-mutants. The discrepancy of cross-resistance pattern of fluopyram with compounds from the same cross-resistance group probably results from the higher intrinsic activity observed for this fungicide and this also suggests that the binding site of fluopyram in complex II may slightly differ from that of other SDHI fungicides and that additional unique mechanism of resistance to fluopyram may arise. Another publication by the same author (Avenot, H F et al., Pest Manag Sci 2011, (wileyonlinelibrary.com) DOI 10.1002/ps. 2311) pertains to the Molecular characterization of boscalid- and penthiopyrad-resistant isolates of *Didymella bryoniae* causing gummi stem blight and assessment of their sensitivity to fluopyram.

The use of a fungicidal composition comprising fluopyram and at least one further succinate dehydrogenase (SDH) inhibitor for improving growth in crops, wherein the improvement is characterized by at least one of the effects of the group consisting of preventively and/or curatively controlling pathogenic fungi and/or nematodes, resistance management, and improved plant physiology effects selected from enhanced root growth, improved greening, improved water use efficiency, improved nitrogen-use efficiency, delayed senescence and enhanced yield is neither described nor suggested in these publications.

It is always of high interest in agriculture to provide novel pesticidal combinations or novel active compound compositions with improved effects for use in protecting crops and improving plant growth and improving plant physiology effects. In this context special focus is put on improved fungicidal activity and synergistic effects of such novel active compound compositions as well as on the combination of a fast efficiency besides a long lasting efficiency to provide increased flexibility with regard to the time of application. In this context, one aim is to provide a new active compound composition, which allows application of the composition when the plant has already been infested with the pathogens and thus achieve a curative effect.

A further aspect with respect to improved efficiency of such novel compound compositions comprises minimization of the doses of chemical products spread in the environment and reduction of the costs of the treatment.

SUMMARY

It was the object of the present invention to provide novel active compound compositions with superior effects in protecting crops and improving plant growth and to provide a new application spectrum by identifying new uses of such active compound compositions.

DETAILED DESCRIPTION OF A PREFERRED EMBODIMENT

The problem underlying the present invention has been solved by providing novel active compound combinations comprising (A) fluopyram and (B) bixafen and (C) at least one triazole fungicide and by providing new use of fungicide compositions comprising (A) fluopyram, (B) at least one further succinate dehydrogenase (SDH) inhibitor and optionally further (C) at least one triazole fungicide for improving growth in crops, wherein the improvement is characterized by at least one of the effects of the group consisting of preventively and/or curatively controlling pathogenic fungi and/or nematodes, resistance management and improving plant physiology effects by enhancing root growth, improving greening, improving water use efficiency, improving nitrogen-use efficacy, delaying senescence and enhancing yield. According to a preferred embodiment of the present invention, the compositions used for improving growth in crops comprise (A) fluopyram, (B) at least one further succinate dehydrogenase (SDH) inhibitor and further (C) at least one triazole fungicide. Most preferably, the at least one triazole fungicide of the active compound combinations is prothioconazole.

In the context of the present invention (A) fluopyram (1.1) refers to a compound of the formula

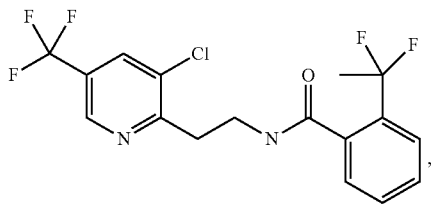 [SMILES: CC(F)(F)c1ccccc1C(=O)NCCc1ncc(C(F)(F)F)cc1Cl]

also known as N-{2-[3-chloro-5-(trifluoromethyl)-2-pyridyl]ethyl}-α,α,α-trifluoro-ortho-toluamide or N-[2-[3-chloro-5-(trifluoromethyl)-2-pyridinyl]ethyl]-2-(trifluoromethyl)benzamide Fluopyram is widely known as a fungicide, belonging to the group of succinate dehydrogenase (SDH) inhibitors. In the context of the present invention it was surprisingly found that fluopyram exhibits a different resistance pattern than other SDH inhibitors (SDHI) such as for example bixafen, which enlarges the spectrum of disease control and allows additional curative effects due to its fast activity.

In the context of the present invention a succinate dehydrogenase (SDH) inhibitor refers to a compound which is capable of inhibiting succinate dehydrogenase in phytopathogenic fungal organisms, also being known as complex II inhibitor. According to the present invention the at least one SDH inhibitor may be selected from the group comprising bixafen (2.1), penflufen (2.2), sedaxane (2.3), isopyrazam (comprising mixture of syn-epimeric racemate 1RS,4SR,9RS and anti-epimeric racemate 1RS,4SR,9SR, anti-epimeric racemate 1RS,4SR,9SR, anti-epimeric enantiomer 1R,4S,9S, anti-epimeric enantiomer 1S,4R,9R, syn epimeric racemate 1RS,4SR,9RS, syn-epimeric enantiomer 1R,4S,9R, syn-epimeric enantiomer 1S,4R,9S) (2.4), penthiopyrad (2.5), furametpyr (2.6), boscalid (2.7), fluxapyroxad (2.8), N-[1-(2,4-dichlorophenyl)-1-methoxypropan-2-yl]-3-(difluoromethyl)-1-methyl-1H-pyrazole-4-carboxamide (2.9), N-[9-(dichloromethylen)-1,2,3,4-tetrahydro-1,4-methanonaphthalen-5-yl]-3-(difluoromethyl)-1-methyl-1H-pyrazol-4-carboxamide (2.10), N-[(1S,4R)-9-(dichloromethylen)-1,2,3,4-tetrahydro-1,4-methanonaphthalen-5-yl]-3-(difluoromethyl)-1-methyl-1H-pyrazol-4-carboxamide (2.11), N-[(1R,4S)-9-(dichloromethylen)-1,2,3,4-tetrahydro-1,4-methanonaphthalen-5-yl]-3-(difluoromethyl)-1-methyl-1H-pyrazol-4-carboxamide (2.12), 3-(difluoromethyl)-1-methyl-N-[2-(1,1,2,2-tetrafluoroethoxy)phenyl]-1H-pyrazol-4-carboxamide (2.13), 3-(difluoromethyl)-N-[4-fluoro-2-(1,1,2,3,3,3-hexafluoropropoxy)phenyl]-1-methyl-1H-pyrazol-4-carboxamide (2.14), 3-(difluoromethyl)-1-methyl-N-[2-(1,1,2,3,3,3-hexafluoropropoxy)phenyl]-1-methyl-1H-pyrazol-4-carboxamide (2.15), 3-(difluoromethyl)-1-methyl-N-[2-(3-Cl-1,1,2-trifluoroethoxy)phenyl]-1H-pyrazol-4-carboxamide (2.16), N-[9-(dichloromethylene)-1,2,3,4-tetrahydro-1,4-methanonaphthalen-5-yl]-3-(difluoromethyl)-1-methyl-1H-pyrazole-4-carboxamide (2.17), N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide (2.18), and N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide (2.19).

Preferably, at least one SDH inhibitor is selected from the group consisting of bixafen (2.1), isopyrazam (2.4), penthiopyrad (2.5), boscalid (2.7) and fluxapyroxad (2.8). The most preferred SDH inhibitor is bixafen (2.1).

In the context of the present invention the triazole may be selected from the group comprising azaconazole (3.1), bitertanol (3.2), bromuconazole (3.3), cyproconazole (3.4), diclobutrazol (3.5), difenoconazole (3.6), diniconazole (3.7), diniconazole-M (3.8), epoxiconazole (3.9), etaconazole (3.10), fenbuconazole (3.11), fluquinconazole (3.12), flusilazole (3.13), flutriafol (3.14), furconazole (3.15), furconazole-cis (3.16), hexaconazole (3.17), imibenconazole (3.18), ipconazole (3.19), metconazole (3.20), myclobutanil (3.21), paclobutrazol (3.22), penconazole (3.23), propiconazole (3.24), prothioconazole (3.25), quinconazole (3.26), simeconazole (3.27), tebuconazole (3.28), tetraconazole (3.29), triadimefon (3.30), triadimenol (3.31), triticonazole (3.32), uniconazole (3.33), uniconazole-P (3.34), voriconazole (3.35), 1-(4-chlorophenyl)-2-(1H-1,2,4-triazol-1-yl)cycloheptanol (3.36).

Preferably the triazole fungicide is selected from the group consisting of epoxiconazole (3.9), prothioconazole (3.25) and tebuconazole (3.28). More preferably, the triazole fungicide is selected from the group consisting of prothioconazole (3.25) and tebuconazole (3.28). The most preferred triazole fungicide is prothioconazole (3.25).

According to a particularly preferred embodiment of the present invention, the composition used for improving growth in crops comprises (A) fluopyram, (B) bixafen, and (C) prothioconazole.

In this context it is noted that at present, the most preferred triazole fungicide prothioconazole is classified as a triazole fungicide according to the widely accepted so-called FRAC-classification (classification by the Fungicide Resistance Action Committee), although it is considered by the FRAC group to establish a new separate group of fungicides—"triazolinthiones"—, referring to triazole fungicides with a sulphur group such as e.g. prothioconazole. For reasons of clarification, the definition of triazole fungicides according to the present invention explicitly comprises prothioconazole.

Preference is given to the following ternary combinations selected from the group consisting of:
(1.1)+(2.1)+(3.1), (1.1)+(2.1)+(3.2), (1.1)+(2.1)+(3.3), (1.1)+(2.1)+(3.4), (1.1)+(2.1)+(3.5), (1.1)+(2.1)+(3.6), (1.1)+(2.1)+(3.7), (1.1)+(2.1)+(3.8), (1.1)+(2.1)+(3.9), (1.1)+(2.1)+(3.10), (1.1)+(2.1)+(3.11), (1.1)+(2.1)+(3.12), (1.1)+(2.1)+(3.13), (1.1)+(2.1)+(3.14), (1.1)+(2.1)+(3.15), (1.1)+(2.1)+(3.16), (1.1)+(2.1)+(3.17), (1.1)+(2.1)+(3.18), (1.1)+(2.1)+(3.19), (1.1)+(2.1)+(3.20), (1.1)+(2.1)+(3.21), (1.1)+(2.1)+(3.22), (1.1)+(2.1)+(3.23), (1.1)+(2.1)+(3.24), (1.1)+(2.1)+(3.25), (1.1)+(2.1)+(3.26), (1.1)+(2.1)+(3.27), (1.1)+(2.1)+(3.28), (1.1)+(2.1)+(3.29), (1.1)+(2.1)+(3.30), (1.1)+(2.1)+(3.31), (1.1)+(2.1)+(3.32), (1.1)+(2.1)+(3.33), (1.1)+(2.1)+(3.34), (1.1)+(2.1)+(3.35), (1.1)+(2.1)+(3.36), (1.1)+(2.2)+(3.1), (1.1)+(2.2)+(3.2), (1.1)+(2.2)+(3.3), (1.1)+(2.2)+(3.4), (1.1)+(2.2)+(3.5), (1.1)+(2.2)+(3.6), (1.1)+(2.2)+(3.7), (1.1)+(2.2)+(3.8), (1.1)+(2.2)+(3.9), (1.1)+(2.2)+(3.10), (1.1)+(2.2)+(3.11), (1.1)+(2.2)+(3.12), (1.1)+(2.2)+(3.13), (1.1)+(2.2)+(3.14), (1.1)+(2.2)+(3.15), (1.1)+(2.2)+(3.16), (1.1)+(2.2)+(3.17), (1.1)+(2.2)+(3.18), (1.1)+(2.2)+(3.19), (1.1)+(2.2)+(3.20), (1.1)+(2.2)+(3.21), (1.1)+(2.2)+(3.22), (1.1)+(2.2)+(3.23), (1.1)+(2.2)+(3.24), (1.1)+(2.2)+(3.25), (1.1)+(2.2)+(3.26), (1.1)+(2.2)+(3.27), (1.1)+(2.2)+(3.28), (1.1)+(2.2)+(3.29), (1.1)+(2.2)+(3.30), (1.1)+(2.2)+(3.31), (1.1)+(2.2)+(3.32), (1.1)+(2.2)+(3.33), (1.1)+(2.2)+(3.34), (1.1)+(2.2)+(3.35), (1.1)+(2.2)+(3.36), (1.1)+(2.3)+(3.1), (1.1)+(2.3)+(3.2), (1.1)+(2.3)+(3.3), (1.1)+(2.3)+(3.4), (1.1)+(2.3)+(3.5), (1.1)+(2.3)+(3.6), (1.1)+(2.3)+(3.7), (1.1)+(2.3)+(3.8), (1.1)+(2.3)+(3.9),
(1.1)+(2.3)+(3.10), (1.1)+(2.3)+(3.11), (1.1)+(2.3)+(3.12),
(1.1)+(2.3)+(3.13), (1.1)+(2.3)+(3.14), (1.1)+(2.3)+(3.15),
(1.1)+(2.3)+(3.16), (1.1)+(2.3)+(3.17), (1.1)+(2.3)+(3.18),
(1.1)+(2.3)+(3.19), (1.1)+(2.3)+(3.20), (1.1)+(2.3)+(3.21),
(1.1)+(2.3)+(3.22), (1.1)+(2.3)+(3.23), (1.1)+(2.3)+(3.24),
(1.1)+(2.3)+(3.25), (1.1)+(2.3)+(3.26), (1.1)+(2.3)+(3.27),
(1.1)+(2.3)+(3.28), (1.1)+(2.3)+(3.29), (1.1)+(2.3)+(3.30),
(1.1)+(2.3)+(3.31), (1.1)+(2.3)+(3.32), (1.1)+(2.3)+(3.33),
(1.1)+(2.3)+(3.34), (1.1)+(2.3)+(3.35), (1.1)+(2.3)+(3.36),
(1.1)+(2.4)+(3.1), (1.1)+(2.4)+(3.2), (1.1)+(2.4)+(3.3),
(1.1)+(2.4)+(3.4), (1.1)+(2.4)+(3.5), (1.1)+(2.4)+(3.6),
(1.1)+(2.4)+(3.7), (1.1)+(2.4)+(3.8), (1.1)+(2.4)+(3.9),
(1.1)+(2.4)+(3.10), (1.1)+(2.4)+(3.11), (1.1)+(2.4)+(3.12),
(1.1)+(2.4)+(3.13), (1.1)+(2.4)+(3.14), (1.1)+(2.4)+(3.15),
(1.1)+(2.4)+(3.16), (1.1)+(2.4)+(3.17), (1.1)+(2.4)+(3.18),
(1.1)+(2.4)+(3.19), (1.1)+(2.4)+(3.20), (1.1)+(2.4)+(3.21),
(1.1)+(2.4)+(3.22), (1.1)+(2.4)+(3.23), (1.1)+(2.4)+(3.24),
(1.1)+(2.4)+(3.25), (1.1)+(2.4)+(3.26), (1.1)+(2.4)+(3.27),
(1.1)+(2.4)+(3.28), (1.1)+(2.4)+(3.29), (1.1)+(2.4)+(3.30),
(1.1)+(2.4)+(3.31), (1.1)+(2.4)+(3.32), (1.1)+(2.4)+(3.33),
(1.1)+(2.4)+(3.34), (1.1)+(2.4)+(3.35), (1.1)+(2.4)+(3.36),
(1.1)+(2.5)+(3.1), (1.1)+(2.5)+(3.2), (1.1)+(2.5)+(3.3),
(1.1)+(2.5)+(3.4), (1.1)+(2.5)+(3.5), (1.1)+(2.5)+(3.6),
(1.1)+(2.5)+(3.7), (1.1)+(2.5)+(3.8), (1.1)+(2.5)+(3.9),
(1.1)+(2.5)+(3.10), (1.1)+(2.5)+(3.11), (1.1)+(2.5)+(3.12),
(1.1)+(2.5)+(3.13), (1.1)+(2.5)+(3.14), (1.1)+(2.5)+(3.15),
(1.1)+(2.5)+(3.16), (1.1)+(2.5)+(3.17), (1.1)+(2.5)+(3.18),
(1.1)+(2.5)+(3.19), (1.1)+(2.5)+(3.20), (1.1)+(2.5)+(3.21),
(1.1)+(2.5)+(3.22), (1.1)+(2.5)+(3.23), (1.1)+(2.5)+(3.24),
(1.1)+(2.5)+(3.25), (1.1)+(2.5)+(3.26), (1.1)+(2.5)+(3.27),
(1.1)+(2.5)+(3.28), (1.1)+(2.5)+(3.29), (1.1)+(2.5)+(3.30),
(1.1)+(2.5)+(3.31), (1.1)+(2.5)+(3.32), (1.1)+(2.5)+(3.33),
(1.1)+(2.5)+(3.34), (1.1)+(2.5)+(3.35), (1.1)+(2.5)+(3.36),
(1.1)+(2.6)+(3.1), (1.1)+(2.6)+(3.2), (1.1)+(2.6)+(3.3),
(1.1)+(2.6)+(3.4), (1.1)+(2.6)+(3.5), (1.1)+(2.6)+(3.6),
(1.1)+(2.6)+(3.7), (1.1)+(2.6)+(3.8), (1.1)+(2.6)+(3.9),
(1.1)+(2.6)+(3.10), (1.1)+(2.6)+(3.11), (1.1)+(2.6)+(3.12),
(1.1)+(2.6)+(3.13), (1.1)+(2.6)+(3.14), (1.1)+(2.6)+(3.15),
(1.1)+(2.6)+(3.16), (1.1)+(2.6)+(3.17), (1.1)+(2.6)+(3.18),
(1.1)+(2.6)+(3.19), (1.1)+(2.6)+(3.20), (1.1)+(2.6)+(3.21),
(1.1)+(2.6)+(3.22), (1.1)+(2.6)+(3.23), (1.1)+(2.6)+(3.24),
(1.1)+(2.6)+(3.25), (1.1)+(2.6)+(3.26), (1.1)+(2.6)+(3.27),
(1.1)+(2.6)+(3.28), (1.1)+(2.6)+(3.29), (1.1)+(2.6)+(3.30),
(1.1)+(2.6)+(3.31), (1.1)+(2.6)+(3.32), (1.1)+(2.6)+(3.33),
(1.1)+(2.6)+(3.34), (1.1)+(2.6)+(3.35), (1.1)+(2.6)+(3.36),
(1.1)+(2.7)+(3.1), (1.1)+(2.7)+(3.2), (1.1)+(2.7)+(3.3),
(1.1)+(2.7)+(3.4), (1.1)+(2.7)+(3.5), (1.1)+(2.7)+(3.6),
(1.1)+(2.7)+(3.7), (1.1)+(2.7)+(3.8), (1.1)+(2.7)+(3.9),
(1.1)+(2.7)+(3.10), (1.1)+(2.7)+(3.11), (1.1)+(2.7)+(3.12),
(1.1)+(2.7)+(3.13), (1.1)+(2.7)+(3.14), (1.1)+(2.7)+(3.15),
(1.1)+(2.7)+(3.16), (1.1)+(2.7)+(3.17), (1.1)+(2.7)+(3.18),
(1.1)+(2.7)+(3.19), (1.1)+(2.7)+(3.20), (1.1)+(2.7)+(3.21),
(1.1)+(2.7)+(3.22), (1.1)+(2.7)+(3.23), (1.1)+(2.7)+(3.24),
(1.1)+(2.7)+(3.25), (1.1)+(2.7)+(3.26), (1.1)+(2.7)+(3.27),
(1.1)+(2.7)+(3.28), (1.1)+(2.7)+(3.29), (1.1)+(2.7)+(3.30),
(1.1)+(2.7)+(3.31), (1.1)+(2.7)+(3.32), (1.1)+(2.7)+(3.33),
(1.1)+(2.7)+(3.34), (1.1)+(2.7)+(3.35), (1.1)+(2.7)+(3.36),
(1.1)+(2.8)+(3.1), (1.1)+(2.8)+(3.2), (1.1)+(2.8)+(3.3),
(1.1)+(2.8)+(3.4), (1.1)+(2.8)+(3.5), (1.1)+(2.8)+(3.6),
(1.1)+(2.8)+(3.7), (1.1)+(2.8)+(3.8), (1.1)+(2.8)+(3.9),
(1.1)+(2.8)+(3.10), (1.1)+(2.8)+(3.11), (1.1)+(2.8)+(3.12),
(1.1)+(2.8)+(3.13), (1.1)+(2.8)+(3.14), (1.1)+(2.8)+(3.15),
(1.1)+(2.8)+(3.16), (1.1)+(2.8)+(3.17), (1.1)+(2.8)+(3.18),
(1.1)+(2.8)+(3.19), (1.1)+(2.8)+(3.20), (1.1)+(2.8)+(3.21),
(1.1)+(2.8)+(3.22), (1.1)+(2.8)+(3.23), (1.1)+(2.8)+(3.24),
(1.1)+(2.8)+(3.25), (1.1)+(2.8)+(3.26), (1.1)+(2.8)+(3.27),
(1.1)+(2.8)+(3.28), (1.1)+(2.8)+(3.29), (1.1)+(2.8)+(3.30),
(1.1)+(2.8)+(3.31), (1.1)+(2.8)+(3.32), (1.1)+(2.8)+(3.33),
(1.1)+(2.8)+(3.34), (1.1)+(2.8)+(3.35), (1.1)+(2.8)+(3.36),
(1.1)+(2.9)+(3.1), (1.1)+(2.9)+(3.2), (1.1)+(2.9)+(3.3),
(1.1)+(2.9)+(3.4), (1.1)+(2.9)+(3.5), (1.1)+(2.9)+(3.6),
(1.1)+(2.9)+(3.7), (1.1)+(2.9)+(3.8), (1.1)+(2.9)+(3.9),
(1.1)+(2.9)+(3.10), (1.1)+(2.9)+(3.11), (1.1)+(2.9)+(3.12),
(1.1)+(2.9)+(3.13), (1.1)+(2.9)+(3.14), (1.1)+(2.9)+(3.15),
(1.1)+(2.9)+(3.16), (1.1)+(2.9)+(3.17), (1.1)+(2.9)+(3.18),
(1.1)+(2.9)+(3.19), (1.1)+(2.9)+(3.20), (1.1)+(2.9)+(3.21),
(1.1)+(2.9)+(3.22), (1.1)+(2.9)+(3.23), (1.1)+(2.9)+(3.24),
(1.1)+(2.9)+(3.25), (1.1)+(2.9)+(3.26), (1.1)+(2.9)+(3.27),
(1.1)+(2.9)+(3.28), (1.1)+(2.9)+(3.29), (1.1)+(2.9)+(3.30),
(1.1)+(2.9)+(3.31), (1.1)+(2.9)+(3.32), (1.1)+(2.9)+(3.33),
(1.1)+(2.9)+(3.34), (1.1)+(2.9)+(3.35), (1.1)+(2.9)+(3.36),
(1.1)+(2.10)+(3.1), (1.1)+(2.10)+(3.2), (1.1)+(2.10)+(3.3),
(1.1)+(2.10)+(3.4), (1.1)+(2.10)+(3.5), (1.1)+(2.10)+(3.6),
(1.1)+(2.10)+(3.7), (1.1)+(2.10)+(3.8), (1.1)+(2.10)+(3.9),
(1.1)+(2.10)+(3.10), (1.1)+(2.10)+(3.11), (1.1)+(2.10)+(3.12), (1.1)+(2.10)+(3.13), (1.1)+(2.10)+(3.14), (1.1)+(2.10)+(3.15), (1.1)+(2.10)+(3.16), (1.1)+(2.10)+(3.17), (1.1)+(2.10)+(3.18), (1.1)+(2.10)+(3.19), (1.1)+(2.10)+(3.20), (1.1)+(2.10)+(3.21), (1.1)+(2.10)+(3.22), (1.1)+(2.10)+(3.23), (1.1)+(2.10)+(3.24), (1.1)+(2.10)+(3.25), (1.1)+(2.10)+(3.26), (1.1)+(2.10)+(3.27), (1.1)+(2.10)+(3.28), (1.1)+(2.10)+(3.29), (1.1)+(2.10)+(3.30), (1.1)+(2.10)+(3.31), (1.1)+(2.10)+(3.32), (1.1)+(2.10)+(3.33), (1.1)+(2.10)+(3.34), (1.1)+(2.10)+(3.35), (1.1)+(2.10)+(3.36), (1.1)+(2.11)+(3.1), (1.1)+(2.11)+(3.2), (1.1)+(2.11)+(3.3), (1.1)+(2.11)+(3.4), (1.1)+(2.11)+(3.5), (1.1)+(2.11)+(3.6), (1.1)+(2.11)+(3.7), (1.1)+(2.11)+(3.8), (1.1)+(2.11)+(3.9), (1.1)+(2.11)+(3.10), (1.1)+(2.11)+(3.11), (1.1)+(2.11)+(3.12), (1.1)+(2.11)+(3.13), (1.1)+(2.11)+(3.14), (1.1)+(2.11)+(3.15), (1.1)+(2.11)+(3.16), (1.1)+(2.11)+(3.17), (1.1)+(2.11)+(3.18), (1.1)+(2.11)+(3.19), (1.1)+(2.11)+(3.20), (1.1)+(2.11)+(3.21), (1.1)+(2.11)+(3.22), (1.1)+(2.11)+(3.23), (1.1)+(2.11)+(3.24), (1.1)+(2.11)+(3.25), (1.1)+(2.11)+(3.26), (1.1)+(2.11)+(3.27), (1.1)+(2.11)+(3.28), (1.1)+(2.11)+(3.29), (1.1)+(2.11)+(3.30), (1.1)+(2.11)+(3.31), (1.1)+(2.11)+(3.32), (1.1)+(2.11)+(3.33), (1.1)+(2.11)+(3.34), (1.1)+(2.11)+(3.35), (1.1)+(2.11)+(3.36), (1.1)+(2.12)+(3.1), (1.1)+(2.12)+(3.2), (1.1)+(2.12)+(3.3), (1.1)+(2.12)+(3.4), (1.1)+(2.12)+(3.5), (1.1)+(2.12)+(3.6), (1.1)+(2.12)+(3.7), (1.1)+(2.12)+(3.8), (1.1)+(2.12)+(3.9), (1.1)+(2.12)+(3.10), (1.1)+(2.12)+(3.11), (1.1)+(2.12)+(3.12), (1.1)+(2.12)+(3.13), (1.1)+(2.12)+(3.14), (1.1)+(2.12)+(3.15), (1.1)+(2.12)+(3.16), (1.1)+(2.12)+(3.17), (1.1)+(2.12)+(3.18), (1.1)+(2.12)+(3.19), (1.1)+(2.12)+(3.20), (1.1)+(2.12)+(3.21), (1.1)+(2.12)+(3.22), (1.1)+(2.12)+(3.23), (1.1)+(2.12)+(3.24), (1.1)+(2.12)+(3.25), (1.1)+(2.12)+(3.26), (1.1)+(2.12)+(3.27), (1.1)+(2.12)+(3.28), (1.1)+(2.12)+(3.29), (1.1)+(2.12)+(3.30), (1.1)+(2.12)+(3.31), (1.1)+(2.12)+(3.32), (1.1)+(2.12)+(3.33), (1.1)+(2.12)+(3.34), (1.1)+(2.12)+(3.35), (1.1)+(2.12)+(3.36), (1.1)+(2.13)+(3.1), (1.1)+(2.13)+(3.2), (1.1)+(2.13)+(3.3), (1.1)+(2.13)+(3.4), (1.1)+(2.13)+(3.5), (1.1)+(2.13)+(3.6), (1.1)+(2.13)+(3.7), (1.1)+(2.13)+(3.8), (1.1)+(2.13)+(3.9), (1.1)+(2.13)+(3.10), (1.1)+(2.13)+(3.11), (1.1)+(2.13)+(3.12), (1.1)+(2.13)+(3.13), (1.1)+(2.13)+(3.14), (1.1)+(2.13)+(3.15), (1.1)+(2.13)+(3.16), (1.1)+(2.13)+(3.17), (1.1)+(2.13)+(3.18), (1.1)+(2.13)+(3.19), (1.1)+(2.13)+(3.20), (1.1)+(2.13)+(3.21), (1.1)+(2.13)+(3.22), (1.1)+(2.13)+(3.23), (1.1)+(2.13)+(3.24), (1.1)+(2.13)+(3.25), (1.1)+(2.13)+(3.26), (1.1)+(2.13)+(3.27), (1.1)+(2.13)+(3.28), (1.1)+(2.13)+(3.29), (1.1)+(2.13)+(3.30), (1.1)+(2.13)+(3.31), (1.1)+(2.13)+(3.32), (1.1)+(2.13)+(3.33), (1.1)+(2.13)+(3.34), (1.1)+(2.13)+

(3.35), (1.1)+(2.13)+(3.36), (1.1)+(2.14)+(3.1), (1.1)+(2.14)+(3.2), (1.1)+(2.14)+(3.3), (1.1)+(2.14)+(3.4), (1.1)+(2.14)+(3.5), (1.1)+(2.14)+(3.6), (1.1)+(2.14)+(3.7), (1.1)+(2.14)+(3.8), (1.1)+(2.14)+(3.9), (1.1)+(2.14)+(3.10), (1.1)+(2.14)+(3.11), (1.1)+(2.14)+(3.12), (1.1)+(2.14)+(3.13), (1.1)+(2.14)+(3.14), (1.1)+(2.14)+(3.15), (1.1)+(2.14)+(3.16), (1.1)+(2.14)+(3.17), (1.1)+(2.14)+(3.18), (1.1)+(2.14)+(3.19), (1.1)+(2.14)+(3.20), (1.1)+(2.14)+(3.21), (1.1)+(2.14)+(3.22), (1.1)+(2.14)+(3.23), (1.1)+(2.14)+(3.24), (1.1)+(2.14)+(3.25), (1.1)+(2.14)+(3.26), (1.1)+(2.14)+(3.27), (1.1)+(2.14)+(3.28), (1.1)+(2.14)+(3.29), (1.1)+(2.14)+(3.30), (1.1)+(2.14)+(3.31), (1.1)+(2.14)+(3.32), (1.1)+(2.14)+(3.33), (1.1)+(2.14)+(3.34), (1.1)+(2.14)+(3.35), (1.1)+(2.14)+(3.36), (1.1)+(2.15)+(3.1), (1.1)+(2.15)+(3.2), (1.1)+(2.15)+(3.3), (1.1)+(2.15)+(3.4), (1.1)+(2.15)+(3.5), (1.1)+(2.15)+(3.6), (1.1)+(2.15)+(3.7), (1.1)+(2.15)+(3.8), (1.1)+(2.15)+(3.9), (1.1)+(2.15)+(3.10), (1.1)+(2.15)+(3.11), (1.1)+(2.15)+(3.12), (1.1)+(2.15)+(3.13), (1.1)+(2.15)+(3.14), (1.1)+(2.15)+(3.15), (1.1)+(2.15)+(3.16), (1.1)+(2.15)+(3.17), (1.1)+(2.15)+(3.18), (1.1)+(2.15)+(3.19), (1.1)+(2.15)+(3.20), (1.1)+(2.15)+(3.21), (1.1)+(2.15)+(3.22), (1.1)+(2.15)+(3.23), (1.1)+(2.15)+(3.24), (1.1)+(2.15)+(3.25), (1.1)+(2.15)+(3.26), (1.1)+(2.15)+(3.27), (1.1)+(2.15)+(3.28), (1.1)+(2.15)+(3.29), (1.1)+(2.15)+(3.30), (1.1)+(2.15)+(3.31), (1.1)+(2.15)+(3.32), (1.1)+(2.15)+(3.33), (1.1)+(2.15)+(3.34), (1.1)+(2.15)+(3.35), (1.1)+(2.15)+(3.36), (1.1)+(2.16)+(3.1), (1.1)+(2.16)+(3.2), (1.1)+(2.16)+(3.3), (1.1)+(2.16)+(3.4), (1.1)+(2.16)+(3.5), (1.1)+(2.16)+(3.6), (1.1)+(2.16)+(3.7), (1.1)+(2.16)+(3.8), (1.1)+(2.16)+(3.9), (1.1)+(2.16)+(3.10), (1.1)+(2.16)+(3.11), (1.1)+(2.16)+(3.12), (1.1)+(2.16)+(3.13), (1.1)+(2.16)+(3.14), (1.1)+(2.16)+(3.15), (1.1)+(2.16)+(3.16), (1.1)+(2.16)+(3.17), (1.1)+(2.16)+(3.18), (1.1)+(2.16)+(3.19), (1.1)+(2.16)+(3.20), (1.1)+(2.16)+(3.21), (1.1)+(2.16)+(3.22), (1.1)+(2.16)+(3.23), (1.1)+(2.16)+(3.24), (1.1)+(2.16)+(3.25), (1.1)+(2.16)+(3.26), (1.1)+(2.16)+(3.27), (1.1)+(2.16)+(3.28), (1.1)+(2.16)+(3.29), (1.1)+(2.16)+(3.30), (1.1)+(2.16)+(3.31), (1.1)+(2.16)+(3.32), (1.1)+(2.16)+(3.33), (1.1)+(2.16)+(3.34), (1.1)+(2.16)+(3.35), (1.1)+(2.16)+(3.36), (1.1)+(2.17)+(3.1), (1.1)+(2.17)+(3.2), (1.1)+(2.17)+(3.3), (1.1)+(2.17)+(3.4), (1.1)+(2.17)+(3.5), (1.1)+(2.17)+(3.6), (1.1)+(2.17)+(3.7), (1.1)+(2.17)+(3.8), (1.1)+(2.17)+(3.9), (1.1)+(2.17)+(3.10), (1.1)+(2.17)+(3.11), (1.1)+(2.17)+(3.12), (1.1)+(2.17)+(3.13), (1.1)+(2.17)+(3.14), (1.1)+(2.17)+(3.15), (1.1)+(2.17)+(3.16), (1.1)+(2.17)+(3.17), (1.1)+(2.17)+(3.18), (1.1)+(2.17)+(3.19), (1.1)+(2.17)+(3.20), (1.1)+(2.17)+(3.21), (1.1)+(2.17)+(3.22), (1.1)+(2.17)+(3.23), (1.1)+(2.17)+(3.24), (1.1)+(2.17)+(3.25), (1.1)+(2.17)+(3.26), (1.1)+(2.17)+(3.27), (1.1)+(2.17)+(3.28), (1.1)+(2.17)+(3.29), (1.1)+(2.17)+(3.30), (1.1)+(2.17)+(3.31), (1.1)+(2.17)+(3.32), (1.1)+(2.17)+(3.33), (1.1)+(2.17)+(3.34), (1.1)+(2.17)+(3.35), (1.1)+(2.17)+(3.36), (1.1)+(2.18)+(3.1), (1.1)+(2.18)+(3.2), (1.1)+(2.18)+(3.3), (1.1)+(2.18)+(3.4), (1.1)+(2.18)+(3.5), (1.1)+(2.18)+(3.6), (1.1)+(2.18)+(3.7), (1.1)+(2.18)+(3.8), (1.1)+(2.18)+(3.9), (1.1)+(2.18)+(3.10), (1.1)+(2.18)+(3.11), (1.1)+(2.18)+(3.12), (1.1)+(2.18)+(3.13), (1.1)+(2.18)+(3.14), (1.1)+(2.18)+(3.15), (1.1)+(2.18)+(3.16), (1.1)+(2.18)+(3.17), (1.1)+(2.18)+(3.18), (1.1)+(2.18)+(3.19), (1.1)+(2.18)+(3.20), (1.1)+(2.18)+(3.21), (1.1)+(2.18)+(3.22), (1.1)+(2.18)+(3.23), (1.1)+(2.18)+(3.24), (1.1)+(2.18)+(3.25), (1.1)+(2.18)+(3.26), (1.1)+(2.18)+(3.27), (1.1)+(2.18)+(3.28), (1.1)+(2.18)+(3.29), (1.1)+(2.18)+(3.30), (1.1)+(2.18)+(3.31), (1.1)+(2.18)+(3.32), (1.1)+(2.18)+(3.33), (1.1)+(2.18)+(3.34), (1.1)+(2.18)+(3.35), (1.1)+(2.18)+(3.36), (1.1)+(2.19)+(3.1), (1.1)+(2.19)+(3.2), (1.1)+(2.19)+(3.3), (1.1)+(2.19)+(3.4), (1.1)+(2.19)+(3.5), (1.1)+(2.19)+(3.6), (1.1)+(2.19)+(3.7), (1.1)+(2.19)+(3.8), (1.1)+(2.19)+(3.9), (1.1)+(2.19)+(3.10), (1.1)+(2.19)+(3.11), (1.1)+(2.19)+(3.12), (1.1)+(2.19)+(3.13), (1.1)+(2.19)+(3.14), (1.1)+(2.19)+(3.15), (1.1)+(2.19)+(3.16), (1.1)+(2.19)+(3.17), (1.1)+(2.19)+(3.18), (1.1)+(2.19)+(3.19), (1.1)+(2.19)+(3.20), (1.1)+(2.19)+(3.21), (1.1)+(2.19)+(3.22), (1.1)+(2.19)+(3.23), (1.1)+(2.19)+(3.24), (1.1)+(2.19)+(3.25), (1.1)+(2.19)+(3.26), (1.1)+(2.19)+(3.27), (1.1)+(2.19)+(3.28), (1.1)+(2.19)+(3.29), (1.1)+(2.19)+(3.30), (1.1)+(2.19)+(3.31), (1.1)+(2.19)+(3.32), (1.1)+(2.19)+(3.33), (1.1)+(2.19)+(3.34), (1.1)+(2.19)+(3.35), (1.1)+(2.19)+(3.36).

Out of these the following combinations are even further preferred:

(1.1)+(2.1)+(3.1), (1.1)+(2.1)+(3.2), (1.1)+(2.1)+(3.3), (1.1)+(2.1)+(3.4), (1.1)+(2.1)+(3.5), (1.1)+(2.1)+(3.6), (1.1)+(2.1)+(3.7), (1.1)+(2.1)+(3.8), (1.1)+(2.1)+(3.9), (1.1)+(2.1)+(3.10), (1.1)+(2.1)+(3.11), (1.1)+(2.1)+(3.12), (1.1)+(2.1)+(3.13), (1.1)+(2.1)+(3.14), (1.1)+(2.1)+(3.15), (1.1)+(2.1)+(3.16), (1.1)+(2.1)+(3.17), (1.1)+(2.1)+(3.18), (1.1)+(2.1)+(3.19), (1.1)+(2.1)+(3.20), (1.1)+(2.1)+(3.21), (1.1)+(2.1)+(3.22), (1.1)+(2.1)+(3.23), (1.1)+(2.1)+(3.24), (1.1)+(2.1)+(3.25), (1.1)+(2.1)+(3.26), (1.1)+(2.1)+(3.27), (1.1)+(2.1)+(3.28), (1.1)+(2.1)+(3.29), (1.1)+(2.1)+(3.30), (1.1)+(2.1)+(3.31), (1.1)+(2.1)+(3.32), (1.1)+(2.1)+(3.33), (1.1)+(2.1)+(3.34), (1.1)+(2.1)+(3.35), (1.1)+(2.1)+(3.36), (1.1)+(2.4)+(3.1), (1.1)+(2.4)+(3.2), (1.1)+(2.4)+(3.3), (1.1)+(2.4)+(3.4), (1.1)+(2.4)+(3.5), (1.1)+(2.4)+(3.6), (1.1)+(2.4)+(3.7), (1.1)+(2.4)+(3.8), (1.1)+(2.4)+(3.9), (1.1)+(2.4)+(3.10), (1.1)+(2.4)+(3.11), (1.1)+(2.4)+(3.12), (1.1)+(2.4)+(3.13), (1.1)+(2.4)+(3.14), (1.1)+(2.4)+(3.15), (1.1)+(2.4)+(3.16), (1.1)+(2.4)+(3.17), (1.1)+(2.4)+(3.18), (1.1)+(2.4)+(3.19), (1.1)+(2.4)+(3.20), (1.1)+(2.4)+(3.21), (1.1)+(2.4)+(3.22), (1.1)+(2.4)+(3.23), (1.1)+(2.4)+(3.24), (1.1)+(2.4)+(3.25), (1.1)+(2.4)+(3.26), (1.1)+(2.4)+(3.27), (1.1)+(2.4)+(3.28), (1.1)+(2.4)+(3.29), (1.1)+(2.4)+(3.30), (1.1)+(2.4)+(3.31), (1.1)+(2.4)+(3.32), (1.1)+(2.4)+(3.33), (1.1)+(2.4)+(3.34), (1.1)+(2.4)+(3.35), (1.1)+(2.4)+(3.36), (1.1)+(2.5)+(3.1), (1.1)+(2.5)+(3.2), (1.1)+(2.5)+(3.3), (1.1)+(2.5)+(3.4), (1.1)+(2.5)+(3.5), (1.1)+(2.5)+(3.6), (1.1)+(2.5)+(3.7), (1.1)+(2.5)+(3.8), (1.1)+(2.5)+(3.9), (1.1)+(2.5)+(3.10), (1.1)+(2.5)+(3.11), (1.1)+(2.5)+(3.12), (1.1)+(2.5)+(3.13), (1.1)+(2.5)+(3.14), (1.1)+(2.5)+(3.15), (1.1)+(2.5)+(3.16), (1.1)+(2.5)+(3.17), (1.1)+(2.5)+(3.18), (1.1)+(2.5)+(3.19), (1.1)+(2.5)+(3.20), (1.1)+(2.5)+(3.21), (1.1)+(2.5)+(3.22), (1.1)+(2.5)+(3.23), (1.1)+(2.5)+(3.24), (1.1)+(2.5)+(3.25), (1.1)+(2.5)+(3.26), (1.1)+(2.5)+(3.27), (1.1)+(2.5)+(3.28), (1.1)+(2.5)+(3.29), (1.1)+(2.5)+(3.30), (1.1)+(2.5)+(3.31), (1.1)+(2.5)+(3.32), (1.1)+(2.5)+(3.33), (1.1)+(2.5)+(3.34), (1.1)+(2.5)+(3.35), (1.1)+(2.5)+(3.36), (1.1)+(2.7)+(3.1), (1.1)+(2.7)+(3.2), (1.1)+(2.7)+(3.3), (1.1)+(2.7)+(3.4), (1.1)+(2.7)+(3.5), (1.1)+(2.7)+(3.6), (1.1)+(2.7)+(3.7), (1.1)+(2.7)+(3.8), (1.1)+(2.7)+(3.9), (1.1)+(2.7)+(3.10), (1.1)+(2.7)+(3.11), (1.1)+(2.7)+(3.12), (1.1)+(2.7)+(3.13), (1.1)+(2.7)+(3.14), (1.1)+(2.7)+(3.15), (1.1)+(2.7)+(3.16), (1.1)+(2.7)+(3.17), (1.1)+(2.7)+(3.18), (1.1)+(2.7)+(3.19), (1.1)+(2.7)+(3.20), (1.1)+(2.7)+(3.21), (1.1)+(2.7)+(3.22), (1.1)+(2.7)+(3.23), (1.1)+(2.7)+(3.24), (1.1)+(2.7)+(3.25), (1.1)+(2.7)+(3.26), (1.1)+(2.7)+(3.27), (1.1)+(2.7)+(3.28), (1.1)+(2.7)+(3.29), (1.1)+(2.7)+(3.30), (1.1)+(2.7)+(3.31), (1.1)+(2.7)+(3.32), (1.1)+(2.7)+(3.33), (1.1)+(2.7)+(3.34), (1.1)+(2.7)+(3.35), (1.1)+(2.7)+(3.36), (1.1)+(2.8)+(3.1), (1.1)+(2.8)+(3.2), (1.1)+(2.8)+(3.3), (1.1)+(2.8)+(3.4), (1.1)+(2.8)+(3.5), (1.1)+(2.8)+(3.6), (1.1)+(2.8)+(3.7), (1.1)+(2.8)+(3.8), (1.1)+(2.8)+(3.9), (1.1)+(2.8)+(3.10), (1.1)+(2.8)+(3.11), (1.1)+(2.8)+(3.12), (1.1)+(2.8)+(3.13), (1.1)+(2.8)+(3.14), (1.1)+(2.8)+(3.15), (1.1)+(2.8)+(3.16), (1.1)+(2.8)+(3.17), (1.1)+(2.8)+(3.18), (1.1)+(2.8)+(3.19), (1.1)+(2.8)+(3.20), (1.1)+(2.8)+(3.21), (1.1)+(2.8)+(3.22), (1.1)+(2.8)+(3.23), (1.1)+(2.8)+(3.24), (1.1)+(2.8)+(3.25), (1.1)+(2.8)+(3.26), (1.1)+(2.8)+(3.27), (1.1)+(2.8)+(3.28), (1.1)+(2.8)+(3.29), (1.1)+(2.8)+(3.30), (1.1)+(2.8)+(3.31), (1.1)+(2.8)+(3.32), (1.1)+(2.8)+(3.33), (1.1)+(2.8)+(3.34), (1.1)+(2.8)+(3.35), (1.1)+(2.8)+(3.36), (1.1)+(2.17)+(3.1), (1.1)+(2.17)+(3.2), (1.1)+(2.17)+(3.3), (1.1)+(2.17)+(3.4), (1.1)+(2.17)+(3.5), (1.1)+(2.17)+(3.6), (1.1)+(2.17)+(3.7), (1.1)+(2.17)+(3.8), (1.1)+(2.17)+(3.9), (1.1)+(2.17)+(3.10), (1.1)+(2.17)+(3.11), (1.1)+(2.17)+(3.12), (1.1)+(2.17)+(3.13), (1.1)+(2.17)+(3.14), (1.1)+(2.17)+(3.15), (1.1)+(2.17)+(3.16), (1.1)+(2.17)+(3.17), (1.1)+(2.17)+(3.18), (1.1)+(2.17)+(3.19), (1.1)+(2.17)+(3.20), (1.1)+(2.17)+(3.21), (1.1)+(2.17)+(3.22), (1.1)+(2.17)+(3.23), (1.1)+(2.17)+(3.24), (1.1)+(2.17)+(3.25), (1.1)+(2.17)+(3.26), (1.1)+(2.17)+(3.27), (1.1)+(2.17)+(3.28), (1.1)+(2.17)+(3.29), (1.1)+(2.17)+(3.30), (1.1)+(2.17)+(3.31), (1.1)+(2.17)+(3.32), (1.1)+(2.17)+(3.33), (1.1)+(2.17)+(3.34), (1.1)+(2.17)+(3.35), (1.1)+(2.17)+(3.36), (1.1)+(2.18)+(3.1), (1.1)+(2.18)+(3.2), (1.1)+(2.18)+(3.3), (1.1)+(2.18)+(3.4), (1.1)+(2.18)+(3.5), (1.1)+(2.18)+(3.6), (1.1)+(2.18)+(3.7), (1.1)+(2.18)+(3.8), (1.1)+(2.18)+(3.9), (1.1)+(2.18)+(3.10), (1.1)+(2.18)+(3.11), (1.1)+(2.18)+(3.12), (1.1)+(2.18)+(3.13), (1.1)+(2.18)+(3.14), (1.1)+(2.18)+(3.15), (1.1)+(2.18)+(3.16), (1.1)+(2.18)+(3.17), (1.1)+(2.18)+(3.18), (1.1)+(2.18)+(3.19), (1.1)+(2.18)+(3.20), (1.1)+(2.18)+(3.21), (1.1)+(2.18)+(3.22), (1.1)+(2.18)+(3.23), (1.1)+(2.18)+(3.24), (1.1)+(2.18)+(3.25), (1.1)+(2.18)+(3.26), (1.1)+(2.18)+(3.27), (1.1)+(2.18)+(3.28), (1.1)+(2.18)+(3.29), (1.1)+(2.18)+(3.30), (1.1)+(2.18)+(3.31), (1.1)+(2.18)+(3.32), (1.1)+(2.18)+(3.33), (1.1)+(2.18)+(3.34), (1.1)+(2.18)+(3.35), (1.1)+(2.18)+(3.36), (1.1)+(2.19)+(3.1), (1.1)+(2.19)+(3.2), (1.1)+(2.19)+(3.3), (1.1)+(2.19)+(3.4), (1.1)+(2.19)+(3.5), (1.1)+(2.19)+(3.6), (1.1)+(2.19)+(3.7), (1.1)+(2.19)+(3.8), (1.1)+(2.19)+(3.9), (1.1)+(2.19)+(3.10), (1.1)+(2.19)+(3.11), (1.1)+(2.19)+(3.12), (1.1)+(2.19)+(3.13), (1.1)+(2.19)+(3.14), (1.1)+(2.19)+(3.15), (1.1)+(2.19)+(3.16), (1.1)+(2.19)+(3.17), (1.1)+(2.19)+(3.18), (1.1)+(2.19)+(3.19), (1.1)+(2.19)+(3.20), (1.1)+(2.19)+(3.21), (1.1)+(2.19)+(3.22), (1.1)+(2.19)+(3.23), (1.1)+(2.19)+(3.24), (1.1)+(2.19)+(3.25), (1.1)+(2.19)+(3.26), (1.1)+(2.19)+(3.27), (1.1)+(2.19)+(3.28), (1.1)+(2.19)+(3.29), (1.1)+(2.19)+(3.30), (1.1)+(2.19)+(3.31), (1.1)+(2.19)+(3.32), (1.1)+(2.19)+(3.33), (1.1)+(2.19)+(3.34), (1.1)+(2.19)+(3.35), (1.1)+(2.19)+(3.36).

Out of the first group the following combinations are also even further preferred:

(1.1)+(2.1)+(3.9), (1.1)+(2.1)+(3.25), (1.1)+(2.1)+(3.28), (1.1)+(2.2)+(3.9), (1.1)+(2.2)+(3.25), (1.1)+(2.2)+(3.28), (1.1)+(2.3)+(3.9), (1.1)+(2.3)+(3.25), (1.1)+(2.3)+(3.28), (1.1)+(2.4)+(3.9), (1.1)+(2.4)+(3.25), (1.1)+(2.4)+(3.28), (1.1)+(2.5)+(3.9), (1.1)+(2.5)+(3.25), (1.1)+(2.5)+(3.28), (1.1)+(2.6)+(3.9), (1.1)+(2.6)+(3.25), (1.1)+(2.6)+(3.28), (1.1)+(2.7)+(3.9), (1.1)+(2.7)+(3.25), (1.1)+(2.7)+(3.28), (1.1)+(2.8)+(3.9), (1.1)+(2.8)+(3.25), (1.1)+(2.8)+(3.28), (1.1)+(2.9)+(3.9), (1.1)+(2.9)+(3.25), (1.1)+(2.9)+(3.28), (1.1)+(2.10)+(3.9), (1.1)+(2.10)+(3.25), (1.1)+(2.10)+(3.28), (1.1)+(2.11)+(3.9), (1.1)+(2.11)+(3.25), (1.1)+(2.11)+(3.28), (1.1)+(2.12)+(3.9), (1.1)+(2.12)+(3.25), (1.1)+(2.12)+(3.28), (1.1)+(2.13)+(3.9), (1.1)+(2.13)+(3.25), (1.1)+(2.13)+(3.28), (1.1)+(2.14)+(3.9), (1.1)+(2.14)+(3.25), (1.1)+(2.14)+(3.28), (1.1)+(2.15)+(3.9), (1.1)+(2.15)+(3.25), (1.1)+(2.15)+(3.28), (1.1)+(2.16)+(3.9), (1.1)+(2.16)+(3.25), (1.1)+(2.16)+(3.28), (1.1)+(2.17)+(3.9), (1.1)+(2.17)+(3.25), (1.1)+(2.17)+(3.28), (1.1)+(2.18)+(3.9), (1.1)+(2.18)+(3.25), (1.1)+(2.18)+(3.28), (1.1)+(2.19)+(3.9), (1.1)+(2.19)+(3.25), (1.1)+(2.19)+(3.28).

Even more preference is given to the following combinations:

(1.1)+(2.1)+(3.9), (1.1)+(2.1)+(3.25), (1.1)+(2.1)+(3.28), (1.1)+(2.4)+(3.9), (1.1)+(2.4)+(3.25), (1.1)+(2.4)+(3.28), (1.1)+(2.5)+(3.9), (1.1)+(2.5)+(3.25), (1.1)+(2.5)+(3.28), (1.1)+(2.7)+(3.9), (1.1)+(2.7)+(3.25), (1.1)+(2.7)+(3.28), (1.1)+(2.8)+(3.9), (1.1)+(2.8)+(3.25), (1.1)+(2.8)+(3.28), (1.1)+(2.17)+(3.9), (1.1)+(2.17)+(3.25), (1.1)+(2.17)+(3.28), (1.1)+(2.18)+(3.9), (1.1)+(2.18)+(3.25), (1.1)+(2.18)+(3.28), (1.1)+(2.19)+(3.9), (1.1)+(2.19)+(3.25), (1.1)+(2.19)+(3.28).

Most preference is given to the following combinations:
(1.1)+(2.1)+(3.25), (1.1)+(2.1)+(3.28), (1.1)+(2.4)+(3.25), (1.1)+(2.4)+(3.28), (1.1)+(2.5)+(3.25), (1.1)+(2.5)+(3.28), (1.1)+(2.7)+(3.25), (1.1)+(2.7)+(3.28), (1.1)+(2.8)+(3.25), (1.1)+(2.8)+(3.28), (1.1)+(2.17)+(3.25), (1.1)+(2.17)+(3.28), (1.1)+(2.18)+(3.25), (1.1)+(2.18)+(3.28), (1.1)+(2.19)+(3.25), (1.1)+(2.19)+(3.28).

There from the combination (1.1)+(2.1)+(3.25) is even most preferred.

Accordingly, an especially preferred embodiment of the present invention refers to compositions, wherein the at least one further SDH inhibitor is bixafen and wherein the triazole fungicide is prothioconazole.

The active compound combinations comprising (A) fluopyram, (B) bixafen and (C) a triazole fungicide according to the present invention may further comprise one or more additional fungicides from the group of succinate dehydrogenase (SDH) inhibitors as defined herein.

Furthermore the active compound combinations and the fungicidal compositions according to the present invention may comprise one or more additional fungicides which may be selected from the group consisting of:

(1) Inhibitors of the ergosterol biosynthesis, for example aldimorph, dodemorph, dodemorph acetate, fenarimol, fenhexamid, fenpropidin, fenpropimorph, flurprimidol, imazalil, imazalil sulfate, naftifine, nuarimol, oxpoconazole, pefurazoate, piperalin, prochloraz, pyributicarb, pyrifenox, spiroxamine, terbinafine, tridemorph, triflumizole, triforine, viniconazole, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H-imidazole-1-carbothioate.

(2) inhibitors of the respiratory chain at complex I or II, for example carboxin, diflumetorim, fenfuram, flutolanil, furmecyclox, mepronil, oxycarboxin, thifluzamide, 1-methyl-N-[2-(1,1,2,2-tetrafluoroethoxy)phenyl]-3-(trifluoromethyl)-1H-pyrazole-4-carboxamide, 5,8-difluoro-N-[2-(2-fluoro-4-{[4-(trifluoromethyl)pyridin-2-yl]oxy}phenyl)ethyl]quinazolin-4-amine (3) inhibitors of the respiratory chain at complex III, for example ametoctradin, amisulbrom, azoxystrobin, cyazofamid, coumethoxystrobin, coumoxystrobin, dimoxystrobin, enestroburin, famoxadone, fenamidone, fenoxystrobin, fluoxastrobin, kresoxim-methyl, metominostrobin, orysastrobin, picoxystrobin, pyraclostrobin, pyrametostrobin, pyraoxystrobin, pyribencarb, triclopyricarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-

[3-(trifluoromethyl)phenyl]ethylidene}amino)oxy] methyl}phenyl)ethanamide, (2E)-2-(methoxyimino)-N-methyl-2-{2-[(E)-({1-[3-(trifluoromethyl)phenyl] ethoxy}imino)methyl]phenyl}ethanamide, (2E)-2-{2-[({[(1E)-1-(3-{[(E)-1-fluoro-2-phenylethenyl] oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy) methyl]phenyl}-2-(methoxyimino)-N-methylethanamide, 2-chloro-N-(1,1,3-trimethyl-2,3-dihydro-1H-inden-4-yl) pyridine-3-carboxamide, 5-methoxy-2-methyl-4-(2-{[({(1E)-1-[3-(trifluoromethyl)phenyl]ethylidene}amino) oxy]methyl}phenyl)-2,4-dihydro-3H-1,2,4-triazol-3-one, methyl (2E)-2-{2-[({cyclopropyl[(4-methoxyphenyl)imino] methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl] phenyl}-2-methoxy-N-methylacetamide and (2R)-2-{2-[(2, 5-dimethylphenoxy)methyl]phenyl}-2-methoxy-N-methylacetamide.

(4) Inhibitors of the mitosis and cell division, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4] triazolo[1,5-a]pyrimidine and 3-chloro-5-(6-chloropyridin-3-yl)-6-methyl-4-(2,4,6-trifluorophenyl)pyridazine.

(5) Compounds capable to have a multisite action, for example bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb and ziram.

(6) Compounds capable to induce a host defence, for example acibenzolar-S-methyl, isotianil, probenazole and tiadinil.

(7) Inhibitors of the amino acid and/or protein biosynthesis, for example andoprim, blasticidin-S, cyprodinil, kasugamycin, kasugamycin hydrochloride hydrate, mepanipyrim, pyrimethanil and 3-(5-fluoro-3,3,4,4-tetramethyl-3,4-dihydroisoquinolin-1-yl)quinoline.

(8) Inhibitors of the ATP production, for example fentin acetate, fentin chloride, fentin hydroxide and silthiofam.

(9) Inhibitors of the cell wall synthesis, for example benthiavalicarb, dimethomorph, flumorph, iprovalicarb, mandipropamid, polyoxins, polyoxorim, validamycin A and valifenalate.

(10) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Inhibitors of the melanine biosynthesis, for example carpropamid, diclocymet, fenoxanil, phthalide, pyroquilon, tricyclazole and 2,2,2-trifluoroethyl {3-methyl-1-[(4-methylbenzoyl)amino]butan-2-yl}carbamate.

(12) Inhibitors of the nucleic acid synthesis, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Inhibitors of the signal transduction, for example chlozolinate, fenpiclonil, fludioxonil, iprodione, procymidone, quinoxyfen and vinclozolin.

(14) Compounds capable to act as an uncoupler, for example binapacryl, dinocap, ferimzone, fluazinam and meptyldinocap.

(15) Further compounds, for example benthiazole, bethoxazin, capsimycin, carvone, chinomethionat, pyriofenone (chlazafenone), cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propanosine-sodium, proquinazid, pyrimorph, (2E)-3-(4-tert-butylphenyl)-3-(2-chloropyridin-4-yl)-1-(morpholin-4-yl)prop-2-en-1-one, (2Z)-3-(4-tert-butylphenyl)-3-(2-chloropyridin-4-yl)-1-(morpholin-4-yl) prop-2-en-1-one, pyrrolnitrine, tebufloquin, tecloftalam, tolnifanide, triazoxide, trichlamide, zarilamid, (3S,6S,7R, 8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl) pyridine, 2,3-dibutyl-6-chlorothieno[2,3-d]pyrimidin-4 (3H)-one, 2,6-dimethyl-1H,5H-[1,4]dithiino[2,3-c:5,6-c'] dipyrrole-1,3,5,7(2H,6H)-tetrone, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1, 3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3-(4,4,5-trifluoro-3,3-dimethyl-3,4-dihydroisoquinolin-1-yl)quinoline, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3, 4-thiadiazole-2-thiol, 5-chloro-N'-phenyl-N'-(prop-2-yn-1-yl)thiophene-2-sulfonohydrazide, 5-fluoro-2-[(4-fluorobenzyl)oxy]pyrimidin-4-amine, 5-fluoro-2-[(4-methylbenzyl)oxy]pyrimidin-4-amine, 5-methyl-6-octyl[1, 2,4]triazolo[1,5-a]pyrimidin-7-amine, ethyl (2Z)-3-amino-2-cyano-3-phenylprop-2-enoate, N'-(4-{[3-(4-chlorobenzyl)-1,2,4-thiadiazol-5-yl]oxy}-2,5-dimethylphenyl)-N-ethyl-N-methylimidoformamide, N-(4-chlorobenzyl)-3-[3-methoxy-4-(prop-2-yn-1-yloxy)phenyl] propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloro-pyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N'-{4-[(3-tert-butyl-4-cyano-1,2-thiazol-5-yl)oxy]-2-chloro-5-methylphenyl}-N-ethyl-N-methylimidoformamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl{6-[({[(1-methyl-1H-tetrazol-5-yl)(phenyl)methylidene]amino}oxy)methyl]pyridin-2-yl}carbamate, phenazine-1-carboxylic acid, quinolin-8-ol, quinolin-8-ol sulfate (2:1) and tert-butyl {6-[({[(1-methyl-1H-tetrazol-5-yl)(phenyl)methylene]amino}oxy)methyl]pyridin-2-yl}carbamate.

(16) Further compounds, for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone, N-[2-(4-{[3-(4-chlorophenyl)prop-2-yn-1-yl]oxy}-3-methoxyphenyl)ethyl]-N2-(methylsulfonyl)valinamide, 4-oxo-4-[(2-phenylethyl)amino]butanoic acid and but-3-yn-1-yl{6-[({[(Z)-(1-methyl-1H-tetrazol-5-yl)(phenyl)methylene]amino}oxy)methyl]pyridin-2-yl}carbamate.

All named combination partners of the classes (1) to (16), as well as the active compound combination and fungicidal composition ingredients (A), (B) and (C) of the present invention can, if their functional groups enable this, optionally form salts with suitable bases or acids.

In context with the present invention improving growth in crops is characterized by at least one of the effects of the group comprising preventively and/or curatively controlling pathogenic fungi and/or nematodes, resistance management, and improving plant physiology effects.

Within the meaning of the present invention, preventive control of pathogenic fungi means that the active compound combinations according to the invention are applied to the seed, the plant, or to fruits of plants prior to the infestation with pathogenic fungi. Curative control of pathogenic fungi means that the active compound combinations according to the invention are applied to the seed, the plant, or to fruits of plants after the infestation with pathogenic fungi.

Resistance management is defined as prevention and/or delay of the development of insensitivity of pathogenic fungi to the fungicidal composition as defined in this invention. Resistance management further refers to the prevention of the loss of a fungicide to agriculture through resistance and aims at prolonging the effectiveness of fungicides liable to encounter resistance problems and to limit crop losses in case resistance appears. Resistance management also refers to strategic measures to avoid or delay the development of resistance with the general goal to prolong the lifetime of a certain active ingredient. As key elements of an anti-resistance strategy may be mentioned:
  to limit the number of treatments per biochemical mode of action,
  to keep the approved application rates,
  to adapt positioning and to give preference to preventive application and avoid treatments under eradicant conditions as a precaution and/or
  to keep the intervals between treatments to avoid selection pressure resulting from under-application in the late stages of persistence of action.

Within the term "resistance", natural resistance is understood as a naturally occurring insensitivity of a pathogen to a group of active ingredients, e.g. fungicides. In contrast, in the case of acquired resistance a pathogen is sensitive to the active ingredient, e.g. a fungicide, before the latter is marketed and used and the selection pressure generated by the active ingredient (e.g. fungicide) reveals and selects a resistant population. According to the scientific definition "resistance" refers to a genetic change predating the active ingredient (e.g. fungicidal) treatment in the plot, which, in response to the selection pressure exerted by this treatment, brings about a reduction in the sensitivity of the pathogen (e.g. fungus) to this active ingredient (e.g. fungicide).

In context with the present invention the term "resistance" comprises natural resistance as well as acquired resistance as described herein and comprises laboratory resistance, which is detected in the laboratory even though the active ingredient (e.g. fungicide) is still effective in the field, as well as practical resistance in the field, which refers to a loss of efficacy observed in the fields and probably confirmed in the laboratory. Especially with respect to resistance against fungi "efficacy of a fungicide" relates to its capacity to inhibit a specific enzyme reaction and "resistance" relates to a loss of fungicidal efficacy, which means, the function concerned is no longer inhibited. In the field of resistance to fungicides, different types of resistance have been described and are comprised from the present invention: within "disruptive resistance" a single target mutation (originating in a single gene) is responsible for a sudden (and probably complete) loss of sensitivity to the fungicide, even if the amount applied is increased, and within "progressive resistance" a sensitivity shift with gradual changes occurs, wherein several mutations (originating in one or more genes) are involved and which results in a slow erosion of sensitivity and thus in a variable degree of resistance.

As key mechanisms for resistance are described:

the target is modified at the site of action of the active ingredient (e.g. fungicide) and therefore the enzyme reaction involved is not inhibited, increased production of the target and therefore the enzyme reaction involved is no longer sufficiently inhibited, the active ingredient (e.g. fungicide) does not reach the target (metabolism, transport, penetration, elimination etc.), the cell sets up a system to offset the target activity of the fungicide.

Therein, as a primary cause of resistance the physical modification of the target at the active ingredient's (e.g. fungicide's) site of action is considered.

Accordingly, in context with the present invention the term "resistance management" means to prevent and/or delay the development of insensitivity of a pathogen (resistance) to an active ingredient or an active compound composition and thus to maintain the efficacy of such active ingredient or active compound composition against the pathogens to be treated.

In principle, well-known standard techniques such as e.g. pyrosequencing for analyzing DNA sequences can be used to detect and identify gene mutations and thus help to correlate such gene mutations to resistance. Thus, DNA analyzes can in principle be helpful in identifying (potentially) resistance relevant gene mutations. Such techniques are well known to a skilled person and widely practiced in the field of resistance management in crops.

Further, in context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance and increased resistance against nematodes Increased plant vigor, comprising plant health/plant quality and seed vigor, reduced stand failure, improved appearance, increased recovery, improved greening effect and improved photosynthetic efficiency.

Effects on plant hormones and/or functional enzymes.

Effects on growth regulators (promoters), comprising earlier germination, better emergence, more developed root system and/or improved root growth, increased ability of tittering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased yield, referring to total biomass per hectare, yield per hectare, kernel/fruit weight, seed size and/or hectolitre weight as well as to increased product quality, comprising:

improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;

further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;

and further comprising decreased undesired ingredients such as e.g. less mycotoxins, less aflatoxins, geosmin level, phenolic aromas, lacchase, polyphenol oxidases and peroxidases, nitrate content etc.

Sustainable agriculture, comprising nutrient use efficiency, especially nitrogen (N)-use efficiency, phosphors (P)-use efficiency, water use efficiency, improved transpiration, respiration and/or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf coloration of the plant and thus comprising colour (greening), water content, dryness etc. Accordingly, in the context of the present invention, it has been found that the specific inventive application of the active compound combination makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composition and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech J. Food Sci.* Vol. 21, No. 3: 91-96, 2000).

Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system"/"improved root growth" refers to longer root system, deeper root growth, faster root growth, higher root dry/fresh weight, higher root volume, larger root surface area, bigger root diameter, higher root stability, more root branching, higher number of root hairs, and/or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m2.

The term "nitrogen-use efficiency" refers technically to the mass of agriculture produce per unit nitrogen consumed and economically to the value of product(s) produced per unit nitrogen consumed, reflecting uptake and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosystem II (PSII). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology,* 2007, 11, 319-341; *Applied Soil Ecology,* 2000, 15, 169-182.)

The improvement in greening/improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photochemical efficiency (Fv/Fm ratio), determination of shoot growth and final root and/or canopy biomass, determination of tiller density as well as of root mortality.

Within the context of the present invention preference is given to improving plant physiology effects which are selected from the group comprising: enhanced root growth/more developed root system, improved greening, improved water use efficiency (correlating to reduced water consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal compositions of the present invention relates to a combined use of a) preventively and/or curatively controlling pathogenic fungi and/or nematodes, with or without resistance management, and b) at least one of enhanced root growth, improved greening, improved water use efficiency, delayed senescence and enhanced yield. From group b) enhancement of root system, water use efficiency and N-use efficiency is particularly preferred.

The combination ratio of the binary and/or ternary combinations according to the present invention is preferably to be chosen such that a synergistic combination is obtained.

In the binary fungicidal combinations according to the invention the compounds (A) and (B) are present in a synergistically effective weight ratio of (A):(B) in a range of 100:1 to 1:100, preferably in a weight ratio of 50:1 to 1:50, most preferably in a weight ratio of 20:1 to 1:20. Further ratios of (A):(B) which can be used according to the present invention with increasing preference in the order given are: 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2. For the binary fungicidal compositions an amount of (A):(B) weight ratio of from 1:0.5 to 1:2, more preferably of from 1:1 is preferred.

In the ternary fungicidal combinations according to the invention the compounds (A) and (B) or the compounds (A) and (C) or the compounds (B) and (C) are present in a synergistically effective weight ratio of A:B or A:C or B:C in a range of 100:1 to 1:100, preferably in a weight ratio of 50:1 to 1:50, most preferably in a weight ratio of 20:1 to 1:20. Further ratios of A:B or A:C or B:C which can be used according to the present invention with increasing preference in the order given are: 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2. For the ternary compositions an amount of (A):(B):(C) weight ratio of from 1:0.5:1 to 1:1.5:3, more preferably of 1:1:2 is preferred.

The active compound combinations and the fungicidal compositions of the present invention may further comprise at least one other additional component such as auxiliaries, solvents, carriers or supports, filler, surfactants or extenders, all being agriculturally acceptable. According to a preferred embodiment of the invention, the active compound combinations and the fungicidal compositions of the present invention further comprise auxiliaries, solvents, carriers, surfactants and/or extenders.

According to the invention the term "support" or "carrier" is to be understood as meaning a natural or synthetic, organic or inorganic substance which is mixed or combined with the active compounds for better applicability, in particular for application to plants or plant parts or seeds. The support or carrier, which may be solid or liquid, is generally inert and should be suitable for use in agriculture. Suitable solid or liquid carriers/supports include for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such supports or carriers. Solid supports/carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks. Suitable liquefied gaseous extenders or carriers are liquids which are gaseous at ambient temperature and under atmospheric pressure, for example aerosol propellants, such as butane, propane, nitrogen and carbon dioxide. Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils and waxes, optionally modified. If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

In the present specification, the term "surfactant" comprises an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

It is further possible to use colourants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

In general, the compositions according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The fungicidal compositions of the present invention can be used for improving growth in crops as defined herein. Thus, according to a further aspect of the present invention, there is provided a method for improving growth in crops according to the aforementioned definition, the method being characterised in that the fungicidal composition as hereinbefore defined is applied to the seed, the plant and/or to the fruit of the plant and/or to the soil in which the plant grows or in which it is supposed to grow, each including seeds of transgenic plants and transgenic plants.

A further aspect of the present invention relates to a method of treating plants, including transgenic plants, in need of better growth, increased harvest yields, a better developed root system, a larger leaf area, greener leaves and/or stronger shoots comprising applying to said plants active compound combinations or fungicidal compositions according to the present invention. Yet another aspect of the present invention relates to a method for improving growth in crops, characterized in that the improved growth is characterized by at least one of the effects of the group consisting of preventively and/or curatively controlling pathogenic fungi and/or nematodes, resistance management, and improved plant physiology effects selected from enhanced root growth, improved greening, improved water use efficiency, improved nitrogen-use efficiency, delayed senescence and enhanced yield. According to a preferred embodiment of the present invention, the method for improving growth in crops is characterized in that the improved growth is characterized by at least one of the effects of the group consisting of better growth, increased harvest yields, a better developed root system, a larger leaf area, greener leaves and stronger shoots.

A further aspect of the present invention relates to a method for improving growth in crops, characterized in that the preventive control of pathogenic fungi and/or nematodes is still observed when the seed or the plant is infested with pathogenic fungi and/or nematodes up to five, preferably four, also preferably three weeks after application of the active compound combinations or fungicidal compositions according to the present invention.

In the context of the present invention, preventive control of pathogenic fungi and/or nematodes up to five, preferably four, also preferably three weeks after application of the active compound combinations or fungicidal compositions according to the present invention means, that the preventive control is still observed when the seeds or plants are infested with pathogenic fungi up to five, preferably four, also preferably three weeks after having been treated with the combinations or compositions of the invention.

In the context of the present invention the term "plant" is to be understood as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant variety protection rights. Parts of plants are to be understood as meaning all above-ground and below-ground parts and organs of the plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example seedlings or seedlings pricking out, plants pricking out, tubers, rhizomes, cuttings and seeds (including seeds of transgenic plants). Preference is given to the treatment of the plants and the above-ground and below-ground parts and organs of the plants, such as shoot, leaf, flower and root, examples which may be mentioned being leaves, needles, stems, trunks, flowers, and fruits, such as ears.

Among the plants that can be treated by the method according to the invention, mention may be made of vegetables: comprising field vegetables as well as root vegetables as e.g. broccoli, cauliflower, cabbage, globe artichokes, Sweet corn (maize), peas, beans, kale, collard greens, spinach, arugula, beet greens, bok choy, chard, choi sum, turnip greens, endive, lettuce, mustard greens, watercress, garlic chives, gai lan, leeks, brussels sprouts, capers, kohlrabi, celery, rhubarb, cardoon, Chinese celery, lemon grass, asparagus, bamboo shoots, galangal, and ginger, potatoes, Jerusalem artichokes, sweet potatoes, taro, yams soybean sprouts, mung beans, urad, alfalfa, carrots, parsnips, beets, radishes, rutabagas, turnips, burdocks, onions, shallots, garlic, tomatoes, cucurbits (cucumbers, squash, pumpkins, melons, luffas, gourds, watermelons), zucchinis peppers, eggplant, tomatillos, christophene, okra, breadfruit and avocado, green beans, lentils and snow peas;

fruits: comprising e.g. tree crops from the group of stone fruits such as e.g. apricots, cherries, almonds, prunes and peaches; tree crops from the group of pome fruits such as e.g. apples and pears; as well as fresh fruits comprising e.g. grapes, berries, citrus, melons and persimmon; and tropical fruits comprising e.g. banana, kiwi, olive, papaya and cacao;

tree crops from the group of nuts such as e.g. Beech, Brazil nut, Candlenut, Cashew, Chestnuts, including Chinese Chestnut, Sweet Chestnut, Colocynth, *Cucurbita ficifolia*, Filbert, Gevuina avellana, Hickory, including Pecan, Shagbark Hickory, Terminalia catappa, Hazelnut, Indian Beech, Kola nut, Macadamia, Malabar chestnut, Pistachio, Mamoncillo, Maya nut, Mongongo, Oak acorns, Ogbono nut, Paradise nut, Pili nut, Walnut, Black Walnut and Water Caltrop;

cereals: comprising e.g. wheat, barley, rye, oat, triticale, millet and rice;

oilseeds: comprising e.g. canola, peanut, sunflower, soybean and oil palm;

sugarcrops: comprising e.g. sugarbeet and sugarcane;

as well as of corn, cotton and coffee.

Preferably the treatment is directed to cereals as defined above, as well as to corn and/or soybeans. Preferably, the cereals are selected from the group consisting of wheat and barley.

The active compound combinations and the fungicidal compositions of the present invention comprise an effective and non-phytotoxic amount of the active ingredients (A), (B) and optionally (C), with the expression "effective and non-phytotoxic amount" means an amount of the ingredients and the active compositions according to the invention which is sufficient to improve growth in crops by preventively and/or curatively controlling or destroying pathogenic fungi and/or nematodes present or liable to appear on the crops, by notably avoiding or controlling the development of resistant strains to the active ingredients, by notably enhancing root growth and/or greening, by notably improving water use efficiency of the crops, by notably delaying senescence by notably enhancing yield and in each case does not entail any appreciable symptom of phytotoxicity for the said crops. Such an amount can vary within a wide range depending on the pathogen to be combated or controlled or the further plant physiology effects to be achieved, the type of crop, the climatic conditions and the compounds included in the fungicidal composition according to the invention. This amount can be determined by systematic field trials, which are within the capabilities of a person skilled in the art.

In the context of the present invention, the term "synergistic effect" is defined by Colby according to the article entitled "Calculation of the synergistic and antagonistic responses of herbicide combinations" Weeds, (1967), 15, pages 20-22.

The active compound combinations and the fungicidal compositions according to the present invention are suitable for the use in the treatment of plants against diseases and pathogenic fungi selected from the group consisting of:

Powdery Mildew Diseases such as *Blumeria* diseases caused for example by *Blumeria graminis*; *Podosphaera* diseases caused for example by *Podosphaera leucotricha*; *Sphaerotheca* diseases caused for example by *Sphaerotheca fuliginea*; *Uncinula* diseases caused for example by *Uncinula necator*;

Rust Diseases such as *Gymnosporangium* diseases caused for example by *Gymnosporangium sabinae*; *Hemileia* diseases caused for example by *Hemileia vastatrix*; *Phakopsora* diseases caused for example by *Phakopsora pachyrhizi* and *Phakopsora meibomiae*; *Puccinia* diseases caused for example by *Puccinia recondita*, *Puccinia graminis* or *Puccinia striiformis*; *Uromyces* diseases caused for example by *Uromyces appendiculatus*;

Oomycete Diseases such as *Albugo* diseases caused for example by *Albugo candida*; *Bremia* diseases caused for example by *Bremia lactucae*; *Peronospora* diseases caused for example by *Peronospora pisi* and *Peronospora brassicae*; *Phytophthora* diseases caused for example by *Phytophthora infestans*;

*Plasmopara* diseases caused for example by *Plasmopara viticola*; *Pseudoperonospora* diseases caused for example by *Pseudoperonospora humuli* and *Pseudoperonospora cubensis*; *Pythium* diseases caused for example by *Pythium ultimum*;

Leaf spot, Leaf blotch and Leaf Blight Diseases such as *Alternaria* diseases caused for example by *Alternaria solani*; *Cercospora* diseases caused for example by *Cercospora beticola*; *Cladosporium* diseases caused for example by *Cladosporium cucumerinum*; *Cochliobolus* diseases caused for example by *Cochliobolus sativus* (Conidiaform: *Drechslera*, Syn: *Helminthosporium*) or *Cochliobolus miyabeanus*; *Colletotrichum* diseases caused for example by *Colletotrichum lindemuthianum*; *Cycloconium* diseases caused for example by *Cycloconium oleaginum*; *Diaporthe* diseases caused for example by *Diaporthe citri*; *Elsinoe* diseases caused for example by *Elsinoe fawcettii*; *Gloeosporium* diseases caused for example by *Gloeosporium laeticolour*; *Glomerella* diseases caused for example by *Glomerella cingulata*; *Guignardia* diseases caused for example by *Guignardia bidwellii*; *Leptosphaeria* diseases caused for example by *Leptosphaeria macularis* and *Leptosphaeria nodorum*; *Magnaporthe* diseases caused for example by *Magnaporthe grisea*; *Mycosphaerella* diseases caused for example by *Mycosphaerella graminicola*, *Mycosphaerella arachidicola* and *Mycosphaerella fijiensis*; *Phaeosphaeria* diseases caused for example by *Phaeosphaeria nodorum*; *Pyrenophora* diseases caused for example by *Pyrenophora teres* or *Pyrenophora tritici repentis*; *Ramularia*-diseases caused for example by *Ramularia collo-cygni* or *Ramularia areola*; *Rhynchosporium* diseases caused for example by *Rhynchosporium secalis*; *Septoria* diseases caused for example by *Septoria apii* and *Septoria lycopersici*; *Typhula* diseases caused for example by *Thyphula incarnata*; *Venturia* diseases caused for example by *Venturia inaequalis*;

Root-, Sheath and Stem Diseases such as *Corticium* diseases caused for example by *Corticium graminearum*; *Fusarium* diseases caused for example by *Fusarium oxysporum*; *Gaeumannomyces* diseases caused for example by *Gaeumannomyces graminis*; *Rhizoctonia* diseases caused for example by *Rhizoctonia solani*; *Sarocladium* diseases caused for example by *Sarocladium oryzae*; *Sclerotium* diseases caused for example by *Sclerotium oryzae*; *Tapesia* diseases caused for example by *Tapesia acuformis*; *Thielaviopsis* diseases caused for example by *Thielaviopsis basicola*;

Ear and Panicle Diseases including Maize cob such as *Alternaria* diseases caused for example by *Alternaria* spp.; *Aspergillus* diseases caused for example by *Aspergillus flavus*; *Cladosporium* diseases caused for example by *Cladosporium cladosporioides*; *Claviceps* diseases caused for example by *Claviceps purpurea*; *Fusarium* diseases caused for example by *Fusarium culmorum*; *Gibberella* diseases caused for example by *Gibberella zeae*; *Monographella* diseases caused for example by *Monographella nivalis*;

Smut- and Bunt Diseases such as *Sphacelotheca* diseases caused for example by *Sphacelotheca reiliana*; *Tilletia* diseases caused for example by *Tilletia caries*; *Urocystis* diseases caused for example by *Urocystis occulta*; *Ustilago* diseases caused for example by *Ustilago nuda*;

Fruit Rot and Mould Diseases such as *Aspergillus* diseases caused for example by *Aspergillus flavus*; *Botrytis* diseases caused for example by *Botrytis cinerea*; *Penicillium* diseases caused for example by *Penicillium expansum* and *Penicillium purpurogenum*; *Rhizopus* diseases caused by example by *Rhizopus stolonifer*. *Sclerotinia* diseases caused for example by *Sclerotinia sclerotiorum*; *Verticillium* diseases caused for example by *Verticillium alboatrum*;

Seed- and Soilborne Decay, Mould, Wilt, Rot and Damping-off diseases such as *Alternaria* diseases caused for example by *Alternaria brassicicola*; *Aphanomyces* diseases caused for example by *Aphanomyces euteiches*; *Ascochyta* diseases caused for example by *Ascochyta lentis*; *Aspergillus* diseases caused for example by *Aspergillus flavus*; *Cladosporium* diseases caused for example by *Cladosporium herbarum*; *Cochliobolus* diseases caused for example by *Cochliobolus sativus*; (Conidiaform: *Drechslera*, *Bipolaris* Syn: *Helminthosporium*); *Colletotrichum* diseases caused for example by *Colletotrichum coccodes*; *Fusarium* diseases caused for example by *Fusarium culmorum*; *Gibberella* diseases caused for example by *Gibberella zeae*; *Macrophomina* diseases caused for example by *Macrophomina phaseolina*; *Microdochium* diseases caused for example by *Microdochium nivale*; *Monographella* diseases caused for example by *Monographella nivalis*; *Penicillium* diseases caused for example by *Penicillium expansum*; *Phoma* diseases caused for example by *Phoma lingam*; *Phomopsis* diseases caused for example by *Phomopsis sojae*; *Phytophthora* diseases caused for example by *Phytophthora cactorum*; *Pyrenophora* diseases caused for example by *Pyrenophora graminea*; *Pyricularia* diseases caused for example by *Pyricularia oryzae*; *Pythium* diseases caused for example by *Pythium ultimum*; *Rhizoctonia* diseases caused for example by *Rhizoctonia solani*; *Rhizopus* diseases caused for example by *Rhizopus oryzae*; *Sclerotium* diseases caused for example by *Sclerotium rolfsii*; *Septoria* diseases caused for example by *Septoria nodorum*; *Typhula* diseases caused for example by *Typhula incarnata*; *Verticillium* diseases caused for example by *Verticillium dahliae*;

Canker, Broom and Dieback Diseases such as *Nectria* diseases caused for example by *Nectria galligena*;

Blight Diseases such as *Monilinia* diseases caused for example by *Monilinia laxa*;

Leaf Blister or Leaf Curl Diseases including deformation of blooms and fruits such as *Exobasidium* diseases caused for example by *Exobasidium vexans*.

*Taphrina* diseases caused for example by *Taphrina deformans*;

Decline Diseases of Wooden Plants such as Esca disease caused for example by *Phaeomoniella clamydospora*, *Phaeoacremonium aleophilum* and *Fomitiporia mediterranea*; *Ganoderma* diseases caused for example by *Ganoderma boninense*; *Rigidoporus* diseases caused for example by *Rigidoporus lignosus*

Diseases of Flowers and Seeds such as *Botrytis* diseases caused for example by *Botrytis cinerea*;

Diseases of Tubers such as *Rhizoctonia* diseases caused for example by *Rhizoctonia solani*; *Helminthosporium* diseases caused for example by *Helminthosporium solani*;

Club root diseases such as *Plasmodiophora* diseases, cause for example by *Plamodiophora brassicae*.

Diseases caused by Bacterial Organisms such as *Xanthomonas* species for example *Xanthomonas campestris* pv. *oryzae*; *Pseudomonas* species for example *Pseudomonas syringae* pv. *lachrymans*; *Erwinia* species for example *Erwinia amylovora*.

The following diseases especially relate to soya beans:

Fungal diseases on leaves, stems, pods and seeds caused, for example, by *alternaria* leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakop-*

*sora meibomiae*), scab (*Sphaceloma glycines*), *stemphylium* leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmopspora vasinfecta*), pod and stem blight (*Diaporthe phaseolorum*), stem canker (*Diaporthe phaseolorum* var. *caulivora*), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), *rhizoctonia* root rot, stem decay, and damping-off (*Rhizoctonia solani*), *sclerotinia* stem decay (*Sclerotinia sclerotiorum*), *sclerotinia* Southern blight (*Sclerotinia rolfsii*), *thielaviopsis* root rot (*Thielaviopsis basicola*).

Preference is given to controlling the following diseases of cereals, especially of wheat, and barley:

Fungal diseases on leaves and stems of wheat are, for example, eyespot (caused by *Tapesia/Oculimacula/Pseudocercosporella* species), *Septoria* leaf blotch (caused by *Septoria tritici*), leaf spot and glume blotch (caused by *Leptosphaeria nodorum*), brown rust (caused by *Puccinia triticiana*), stripe rust (caused by *Puccinia striifomis*), tan spot (caused by *Pyrenophora/Drechslera tritici-repentis*), powdery mildew (caused by *Blumeria graminis/Erysiphe graminis*), and ear blight (caused by *Fusarium* spp.). Fungal diseases on leaves and stems of barley are, for example, eyespot (caused by *Tapesia/Oculimacula/Pseudocercosporella* species), leaf blotch (caused by *Rhynchosporium secalis*), net blotch (caused by *Pyrenophora/Drechslera teres*), brown rust (caused by *Puccinia hordei*), powdery mildew (caused by *Blumeria graminis/Erysiphe graminis*), and *Ramularia* leaf spot (caused by *Ramularia collo-cygni*).

Preferably the active compound combinations and the fungicidal compositions of the present invention are used for controlling pathogenic fungi, selected from the group consisting of *Pyrenophora/Drechslera* (including *Pyrenophora/Drechslera tritici-repentis* and *Pyrenophora/Drechslera teres*), *Septoria* (including *Septoria nodorum, Septoria tritici*), *Puccinia, Erysiphe* (synonym: *Blumeria*), *Leptosphaeria* (including *Leptosphaeria nodorum*) and *Pseudocercosporella* (synonym: *Tapesia/Oculimacula*). Most preferred is the treatment of *Septoria, Pyrenophora* and *Leptosphaeria*, especially *Pyrenophora tritici-repentis, Septoria nodorum, Septoria tritici* and *Leptosphaeria nodorum*. According to an also preferred embodiment of the present invention, the active compound combinations and the fungicidal compositions of the present invention are used for controlling pathogenic fungi, selected from the group consisting of *Tapesia/Oculimacula/Pseudocercosporella* species, *Septoria tritici, Leptosphaeria nodorum, Puccinia triticiana, Puccinia striifomis, Pyrenophora/Drechslera tritici-repentis, Blumeria graminis/Erysiphe graminis, Fusarium* spp., *Rhynchosporium secalis, Pyrenophora/Drechslera teres, Puccinia hordei*, and *Ramularia collo-cygni*.

It is also possible to control resistant strains of the organisms mentioned above.

In a preferred embodiment of the present invention the active compound combinations and the fungicidal compositions are used for the treatment of cereals, preferably selected from wheat and barley.

In a preferred embodiment of the present invention the active compound combinations and the fungicidal compositions are used for the treatment of cereals, especially wheat, against *Pyrenophora* (especially *Pyrenophora tritici-repentis*), *Septoria* (especially *Septoria tritici*), *Puccinia, Erysiphe* (synonym: *Blumeria*), *Leptosphaeria* (especially *Leptosphaeria nodorum*), *Pseudocercosporella* (synonym: *Tapesia/Oculimacula*), with *Septoria, Pyrenophora* and *Leptosphaeria* being most preferred.

It is even more preferred to use the active compound combinations and the fungicidal compositions for the treatment of early and/or late leaf diseases and/or ear diseases of cereals.

According to a further aspect of the present invention the active compound combinations and the fungicidal compositions according to the present invention are suitable for the use in the treatment of plants against nematodes. Nematodes are tiny, worm-like, multicellular animals adapted to living in water. The number of nematode species is estimated at half a million. An important part of the soil fauna, nematodes live in a maze of interconnected channels, called pores, that are formed by soil processes. They move in the films of water that cling to soil particles. Plant-parasitic nematodes, a majority of which are root feeders, are found in association with most plants. Some are endoparasitic, living and feeding within the tissue of the roots, tubers, buds, seeds, etc. Others are ectoparasitic, feeding externally through plant walls. A single endoparasitic nematode can kill a plant or reduce its productivity. Endoparasitic root feeders include such economically important pests as the root-knot nematodes (*Meloidogyne* species), the reniform nematodes (*Rotylenchulus* species), the cyst nematodes (*Heterodera* species), and the root-lesion nematodes (*Pratylenchus* species). Direct feeding by nematodes can drastically decrease a plant's uptake of nutrients and water. Nematodes have the greatest impact on crop productivity when they attack the roots of seedlings immediately after seed germination. Nematode feeding also creates open wounds that provide entry to a wide variety of plant-pathogenic fungi and bacteria. These microbial infections are often more economically damaging than the direct effects of nematode feeding.

Current nematode control focuses essentially on the prevention of nematode attack on the plant. Once a plant is parasitized it is virtually impossible to kill the nematode without also destroying the plant. Therefore, it would be advantageous to provide nematode control compounds and methods of treating plants to prevent or reduce nematode damage.

According to the present invention the nematode species are selected from the group consisting of *Aglenchus agricola, Anguina tritici, Aphelenchoides arachidis, Aphelenchoides fragariae, Belonolaimus gracilis, Belonolaimus longicaudatus, Belonolaimus nortoni, Cacopaurus pestis, Criconemella curvata, Criconemella onoensis, Criconemella ornata, Criconemella rusium, Criconemella xenoplax* (=*Mesocriconema xenoplax*) and *Criconemella* spp. in general, *Criconemoides ferniae, Criconemoides onoense, Criconemoides ornatum* and *Criconemoides* spp. in general, *Ditylenchus destructor, Ditylenchus dipsaci, Ditylenchus myceliophagus* and *Ditylenchus* spp. in general, *Dolichodorus heterocephalus, Globodera pallida* (=*Heterodera pallida*), *Globodera rostochiensis, Globodera solanacearum, Globodera tabacum, Globodera virginiae, Helicotylenchus digonicus, Helicotylenchus dihystera, Helicotylenchus erythrine, Helicotylenchus multicinctus, Helicotylenchus nannus, Helicotylenchus pseudorobustus* and *Helicotylenchus* spp. in general, *Hemicriconemoides, Hemicycliophora* arenaria, Hemicycliophora nudata, Hemicycliophora parvana, Heterodera avenae, Heterodera cruciferae, Heterodera glycines, Heterodera oryzae, Heterodera schachtii, Heterodera zeae and Heterodera spp. in general, Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola and Longidorus spp. in general, Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne naasi, Meloidogyne paranaensis, Meloidogyne thamesi and Meloidogyne spp. in general, Meloinema spp., Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres and Paratrichodorus spp. in general, Paratylenchus hamatus, Paratylenchus minutus, Paratylenchus projectus and Paratylenchus spp. in general, Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae and Pratylenchus spp. in general, Pseudohalenchus minutus, Psilenchus magnidens, Psilenchus tumidus, Punctodera chalcoensis, Quinisulcius acutus, Radopholus citrophilus, Radopholus similis, Rotylenchulus borealis, Rotylenchulus parvus, Rotylenchulus reniformis and Rotylenchulus spp. in general, Rotylenchus laurentinus, Rotylenchus macrodoratus, Rotylenchus robustus, Rotylenchus uniformis and Rotylenchus spp. in general, Scutellonema brachyurum, Scutellonema bradys, Scutellonema clathricaudatum and Scutellonema spp. in general, Subanguina radicicola, Tetylenchus nicotianae, Trichodorus cylindricus, Trichodorus minor, Trichodorus primitivus, Trichodorus proximus, Trichodorus similis, Trichodorus sparsus and Trichodorus spp. in general, Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris and Tylenchorhynchus spp. in general, Tylenchulus semipenetrans, Xiphinema americanum, Xiphinema brevicolle, Xiphinema dimorphicaudatum, Xiphinema index and Xiphinema spp.

Preferably, the nematode species are selected from the group consisting of Aphelenchoides spp., Bursa-phelenchus spp., Ditylenchus spp., Globodera spp., Heterodera spp., Longidorus spp., Meloidogyne spp., Pratylenchus spp., Radopholus spp., Trichodorus spp., Tylenchulus spp, Xiphinema spp., Helicotylenchus spp., Tylenchorhynchus spp., Scutellonema spp., Paratrichodorus spp., Meloinema spp., Paraphelenchus spp., Aglenchus spp., Belonolaimus spp., Nacobbus spp, Rotylenchulus spp., Rotylenchus spp., Neotylenchus spp., Paraphelenchus spp., Dolichodorus spp., Hoplolaimus spp., Punctodera spp., Criconemella spp., Quinisulcius spp., Hemicycliophora spp., Anguina spp., Subanguina spp., Hemicriconemoides spp., Psilenchus spp., Pseudohalenchus spp., Criconemoides spp., Cacopaurus spp.

The combinations according to the present invention are particularly useful in controlling nematodes in corn belonging to at least one species selected from the group of the phytoparasitic nematodes, especially consisting of Belonolaimus longicaudatus, Paratrichodorus minor and also consisting of Pratylenchus brachyurus, Pratylenchus delattrei, Pratylenchus hexincisus, Pratylenchus penetrans, Pratylenchus zeae, (Belonolaimus gracilis), Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum, Subanguina radicicola.

The combinations according to the present invention are particularly useful in controlling nematodes in soybean belonging to at least one species selected from the group of the phytoparasitic nematodes, especially consisting of Pratylenchus brachyurus, Pratylenchus pratensis, Pratylenchus penetrans, Pratylenchus scribneri, Belonolaimus longicaudatus, Heterodera glycines, Hoplolaimus columbus and also consisting of Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus, Rotylenchulus reniformis.

This invention now provides advantageous uses of the active compound combinations and the fungicidal compositions according to the present invention for controlling nematodes infesting crops selected from the group consisting of vegetables, in particular tomato and cucurbits, potato, corn, soy, cotton, tobacco, coffee, fruits, in particular, citrus fruits, pine apples and bananas, and grapes and for increasing yield.

The method of treating plants according to the present invention is characterized in that in the treatment of leaves from 0.1 to 10 000 g active compound combination or fungicidal composition per ha and in the treatment of seed from 2 to 200 g active compound combination or fungicidal composition per 100 kg of seed are employed. It is clearly understood that the doses indicated above are given as illustrative examples of the invention. A person skilled in the art will know how to adapt the application doses according to the nature of the crop, the disease, the pathogenic fungi and/or nematodes to be treated or any other growth improving effect to be achieved.

Preferred dosages comprise 75 g/ha fluopyram, 75 g/ha of the further SDH inhibitor (preferably bixafen) and, if present, 150 g/ha of the triazole fungicide (preferably prothioconazole).

The compositions according to the present invention may also be used for the preparation of compositions useful to curatively or preventively treat human and animal fungal diseases such as, for example, mycoses, dermatoses, trichophyton diseases and candidiases or diseases caused by Aspergillus spp. or Candida spp., for example Aspergillus fumigatus or Candida albicans respectively.

According to the present invention, a synergistic effect of e.g. fungicides is always present when the fungicidal activity of the active compound combinations exceeds the total of the activities of the active compounds when applied individually. The expected activity for a given combination of two active compounds (binary composition) can be calculated as follows:

$$E = x + y - \frac{x * y}{100}$$

in which E represents the expected percentage of inhibition of the disease for the combination of two fungicides at defined doses (for example equal to x and y respectively), x is the percentage of inhibition observed for the disease by the compound (A) at a defined dose (equal to x), y is the percentage of inhibition observed for the disease by the compound (B) at a defined dose (equal to y). When the percentage of inhibition observed for the combination is greater than E, there is a synergistic effect.

The expected activity for a given combination of three active compounds (ternary composition) can be calculated as follows:

$$E = X + Y + Z - \left(\frac{X \cdot Y + X \cdot Z + Y \cdot Z}{100}\right) + \frac{X \cdot Y \cdot Z}{10000}$$

wherein

X is the efficacy when active compound A is applied at an application rate of m ppm (or g/ha), Y is the efficacy when active compound B is applied at an application rate of n ppm (or g/ha), Z is the efficacy when active compound C is applied at an application rate of r ppm (or g/ha), E is the efficacy when the active compounds A, B and C are applied at application rates of m, n and r ppm (or g/ha), respectively.

The degree of efficacy, expressed in % is denoted. 0% means an efficacy which corresponds to that of the control while an efficacy of 100% means that no disease is observed.

If the actual activity exceeds the calculated value, then the activity of the combination is superadditive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, a graphic representation of synergism in pesticides" in *Neth. J. Plant Path.,* 1964, 70, 73-80).

The present invention will now be illustrated with the following examples:

EXAMPLES

Example 1

Synergistic Effect in Field Trials in Winter Wheat

The advanced fungicidal activity of the active compound combinations according to the invention is evident from the example below. While the individual active compounds exhibit weaknesses with regard to the fungicidal activity, the combinations have an activity which exceeds a simple addition of activities.

Field trials in winter wheat were conducted in the year 2010 in France and Germany. The trials have been conducted according to approved guidelines (EPPO). The spray volumes were in line with farmers' practice, varying from 250-300 l/ha.

TABLE 1

Field trials conducted in wheat (France and Germany; 2010).

| Trial | Crop | Country | Guide-line | Plot Size m²/rep. | Cultivar | No. of appl. | BBCH |
|---|---|---|---|---|---|---|---|
| FRA-AJ28 | Wheat | France | EPPO | 12 | Tanker | 2 | 32-45 |
| DEU-S826 | Wheat | Germany | EPPO | 10 | Ritmo | 2 | 32-49 |
| DEU-NWU3 | Wheat | Germany | EPPO | 12, 5 | Biscay | 2 | 32-39 |

BBCH: The BBCH-scale is a well-known scale used to identify the phenological development stages of a plant.

Products respectively formulated compound or compound combination:

(I) Bixafen EC125,
(II) Fluopyram EC200,
(III) Prothioconazole EC200,
(I)+(II)+(III) Bixafen & Fluopyram EC200+Prothioconazole EC200
(a.i. ratio=1:1:2).

Example 1A

*Septoria tritici* Test (Wheat)

To test for fungicide activity against *Septoria tritici* (SEPTTR), the plots of the field trial FRA-AJ28 (variety Aubusson) are sprayed twice with the formulated active compound or the formulated active compound combination at the stated rate of application.

Active compounds/formulations:

Bixafen EC125 (I),
Fluopyram EC200 (II),
Prothioconazole EC200 (III),
Bixafen+Fluopyram EC200+Prothioconazole EC200
[a.i. ratio Bixafen (I):Fluopyram (II):Prothioconazole (III)= 1:1:2].

The test is evaluated 47 days after the second application (47DAB/growth stage BBCH 77).

0% means an efficacy which corresponds to that of the untreated control, while an efficacy of 100% means that no disease is observed.

TABLE 2

Efficacy against *Septoria tritici* (47DAB) under field conditions (trial FRA-AJ28).

Trial: FRA-AJ28
Crop Stage (BBCH): 77
DAA: 69
DAB: 47
Target (Pathogen): SEPTTR
Variety: Aubusson
Plant Part Rated: LEAF

| Active compounds | Application rate of active compound [g/ha] | Rating Scale: % Rating Type: Mean | Tukey[1] | % ABBOTT | Efficacy [%] % found* | % calc.** |
|---|---|---|---|---|---|---|
| Untreated control | 0 | 95.0 | a | — | | |
| (I) Bixafen | 75 | 36.3 | de | 61.8 | 61.8 | |
| (II) Fluopyram | 75 | 52.5 | bc | 44.7 | 44.7 | |
| (III) Prothioconazole | 150 | 30.0 | e | 68.4 | 68.4 | |
| (I) + (II) + (III) 1:1:2 | 75 + 75 + 150 | 4.5 | h | 95.3 | 95.3 | 93.3 |

DAA = Days after first treatment (application)
DAB = Days after second treatment
*found = activity found/
**calc. = activity
[1]Means with the same letter are not significantly different

Example 1B

*Leptosphaeria nodorum* Test (Wheat)

To test for fungicide activity against *Leptosphaeria nodorum* (LEPTNO), the plots of the field trial DEU-S826 (variety Ritmo) are sprayed twice with the formulated active compound or the formulated active compound combination at the stated rate of application.

Active compounds/formulations:
Bixafen EC125 (I),
Fluopyram EC200 (II),
Prothioconazole EC200 (III),
Bixafen+Fluopyram EC200+Prothioconazole EC200
[a.i. ratio Bixafen (I):Fluopyram (II):Prothioconazole (III)= 1:1:2].

The test is evaluated 18 days after the second application (18DAB/growth stage BBCH 69).

0% means an efficacy which corresponds to that of the untreated control, while an efficacy of 100% means that no disease is observed.

TABLE 3

Efficacy against *Leptosphaeria nodorum* (18DAB) under field conditions (trial DEU-S826).

Trial: DEU-S826
Crop Stage (BBCH): 69
DAA: 46
DAB: 18
Target (Pathogen): LEPTNO
Variety: Ritmo
Plant Part Rated: LEALOW

| Active compounds | Application rate of active compound [g/ha] | Rating Scale: % Rating Type: Mean | Tukey[1] | % ABBOTT | Efficacy [%] % found* | % calc.** |
|---|---|---|---|---|---|---|
| Untreated control | 0 | 23.1 | a | — | | |
| (I) Bixafen | 75 | 14.7 | b | 36.5 | 36.5 | |
| (II) Fluopyram | 75 | 10.9 | be | 53.0 | 53.0 | |
| (III) Prothioconazole | 150 | 6.4 | bcd | 72.4 | 72.4 | |
| (I) + (II) + (III) 1:1:2 | 75 + 75 + 150 | 0.8 | h | 96.4 | 96.4 | 91.8 |

DAA = Days after first treatment (application)
DAB = Days after second treatment
LEALOW = Leaf – Lower (lower leave parts)
*found = activity found/
**calc. = activity
[1]Means with the same letter are not significantly different

Example 1C

Pyrenophora tritici-repentis Test (wheat)

To test for fungicide (protectant) activity against *Pyrenophora tritici-repentis* (PYRNTR), the plots of the field trial DEU-NWU3 (variety Biscay) are sprayed twice with the formulated active compound or the formulated active compound combination at the stated rate of application.

Active compounds/formulations:
Bixafen EC125 (I),
Fluopyram EC200 (II),
Prothioconazole EC200 (III),
Bixafen+Fluopyram EC200+Prothioconazole EC200
[a.i. ratio Bixafen (I):Fluopyram (II):Prothioconazole (III)= 1:1:2].

The test is evaluated 43 days after the second application (43DAB/growth stage BBCH 83). 0% means an efficacy which corresponds to that of the untreated control, while an efficacy of 100% means that no disease is observed.

TABLE 4

Efficacy against *Pyrenophora tritici*-repentis (43DAB) under field conditions (trial DEU-NWU3).

Trial: DEU-NWU3
Crop Stage (BBCH): 83
DAA: 61
DAB: 43
Target (Pathogen): PYRNTR
Variety: Biscay
Plant Part Rated: FL-0-1

| Active compounds | Application rate of active compound [g/ha] | Rating Scale: % Rating Type: Mean | Tukey[1] | % ABBOTT | Efficacy [%] % found* | % calc.** |
|---|---|---|---|---|---|---|
| Untreated control | 0 | 2.8 | a | — | | |
| (I) Bixafen | 75 | 2.3 | ab | 18.2 | 18.2 | |
| (II) Fluopyram | 75 | 2.3 | ab | 18.2 | 18.2 | |
| (III) Prothioconazole | 150 | 1.8 | ab | 36.4 | 36.4 | |
| (I) + (II) + (III) 1:1:2 | 75 + 75 + 150 | 0.5 | c | 81.8 | 81.8 | 57.4 |

DAA = Days after first treatment (application)
DAB = Days after second treatment
FL-0-1 = Flagleaf + FL-1
*found = activity found/
**calc. = activity
[1]Means with the same letter are not significantly different

Example 2

Characterization of Protective and Curative Potential of Active Compound Combinations of the Present Invention in Controlling *Septoria tritici* in Winter Wheat Materials and Methods:
Crop: winter wheat (cv. Monopol)
Cultivation: Seeding at 10° C.; 80% rel. humidity; 12 h artificial lighting; 10-15 seeds per pot (pot volume 6×6 cm); substrate: peat soil with fertilizer
Greenhouse conditions during the trial: 15° C., 60% rel. humidity
Application: Spray application in slide spraying cabin; Preventive: 11, 8, 4, 1 dbi [days before inoculation]; Curative: 1, 4, 8, 11 dai [days after inoculation]
Application volume: 250 l/ha
Speed of spray boom: 22 m/min, distance to plant: 50 cm Inoculation: *Septoria tritici* (*Mycosphaerella graminicola*); Spore suspension of cryopreservated spores; (conc. $10^6$ Spores/ml)
Assessment: 21 day after inoculation; Estimation of infested leaf area (ABBOTT %); Quantification of *Septoria*-DNA (SeptoCast)

TABLE 5

Treatment List:

| Treatment | Product | Formulation | Dose rate [l/ha] |
|---|---|---|---|
| 1 | UTC | — | — |
| 2 | BIX | 125 EC | 0.6 |
| 3 | BIX + FLU | 200 EC (100 + 100) | 0.75 |
| 4 | BIX + PTZ | 225 EC (75 + 150) | 1 |
| 5 | BIX + FLU + PTZ | 300 EC (75 + 75 + 150) | 1 |

TABLE 5-continued

Treatment List:

| Treatment | Product | Formulation | Dose rate [l/ha] |
|---|---|---|---|
| 6 | IZM + ECA | 125 EC + 125 SC | 0.6 + 1.2 |
| 7 | IZM + ECA | 125 EC + 125 SC | 1 + 0.5 |

UTC = untreated control;
FLU = Fluopyram;
BIX = Bixafen;
PTZ = Prothioconazole;
IZM = Isopyrazam;
ECA = Epoxiconazole Results Preventive (Protective) Potential:

TABLE 6

| Visual assessment (Results are given in [%] ABBOTT) | | | | |
|---|---|---|---|---|
| Compound | 11 dbi | 8 dbi | 4 dbi | 1 dbi |
| BIX | 88.7 | 96.7 | 100 | 100 |
| BIX/FLU | 96.7 | 100 | 100 | 100 |
| BIX/PTZ | 96.7 | 100 | 100 | 100 |
| BIX/FLU/PTZ | 99.5 | 100 | 100 | 100 |
| IZM/ECA 0.6/1.2 | 100 | 99.1 | 100 | 100 |
| IZM/ECA 1.0/0.5 | 96.9 | 98.5 | 99.1 | 100 | dbi = days before inoculation
BIX + FLU demonstrated a significant better protective potential than BIX straight.
BIX + FLU + PTZ was slightly superior to BIX + PTZ.

The protective potential of BIX-combinations was comparable to IZM-combinations.

TABLE 7

| DNA Quantification [Septoria DNA] (Results refer to relative copy numbers [n]) | | | | |
|---|---|---|---|---|
| Compound | 11 dbi | 8 dbi | 4 dbi | 1 dbi |
| BIX | 2853 | 428 | 141 | 120 |
| BIX/FLU | 598 | 284 | 121 | 89 |
| BIX/PTZ | 369 | 253 | 227 | 138 |
| BIX/FLU/PTZ | 253 | 144 | 60 | 60 |
| IZM/ECA 0.6/1.2 | 535 | 413 | 192 | 195 |
| IZM/ECA 1.0/0.5 | 2006 | 436 | 998 | 149 |

BIX + FLU demonstrated better protective potential than BIX as solo compound.
BIX + FLU + PTZ demonstrated improved protective activity, slightly superior to BIX + PTZ.
Both IZM combinations were inferior to BIX/FLU/PTZ and BIX/PTZ.

Results Curative Potential:

TABLE 8

| Visual assessment (Results are given in [%] ABBOTT) | | | | |
|---|---|---|---|---|
| Compound | 1 dai | 4 dai | 8 dai | 11 dai |
| BIX | 100 | 100 | 81.1 | 80.2 |
| BIX/FLU | 100 | 100 | 100 | 100 |
| BIX/PTZ | 100 | 100 | 100 | 92.6 |
| BIX/FLU/PTZ | 100 | 100 | 100 | 98.6 |
| IZM/ECA 0.6/1.2 | 100 | 100 | 100 | 100 |
| IZM/ECA 1.0/0.5 | 100 | 100 | 100 | 96.8 | dai = days after inoculation
BIX + FLU demonstrated a significantly better curative potential than BIX as solo compound.
BIX + FLU, BIX + FLU + PTZ and IZM + ECA showed improved curative activities.
BIX + PTZ was inferior to BIX + FLU and BIX + FLU + PTZ.

TABLE 9

| DNA Quantification [Septoria DNA] (Results refer to relative copynumbers [n]) | | | | |
|---|---|---|---|---|
| Compound | 1 dai | 4 dai | 8 dai | 11 dai |
| BIX | 135 | 416 | 10421 | 19806 |
| BIX/FLU | 142 | 126 | 263 | 372 |
| BIX/PTZ | 118 | 135 | 176 | 404 |
| BIX/FLU/PTZ | 79 | 143 | 192 | 317 |

TABLE 9-continued

| DNA Quantification [Septoria DNA] (Results refer to relative copynumbers [n]) | | | | |
|---|---|---|---|---|
| Compound | 1 dai | 4 dai | 8 dai | 11 dai |
| IZM/ECA 0.6/1.2 | 100 | 284 | 76 | 392 |
| IZM/ECA 1.0/0.5 | 105 | 119 | 101 | 985 |

BIX + FLU demonstrated a significant better curative potential than BIX straight.
BIX + FLU + PTZ showed an improved curativity, slightly superior to BIX + PTZ, BIX + FLU and IZM + ECA (0.6/1.2).

Conclusion:

The ternary combination BIX/FLU/PTZ demonstrated the best protective and curative activity, hence providing the highest flexibility regarding the application to control *S. tritici*.

The protective and curative characteristics of BIX/PTZ are comparable to the tested IZM combinations.

BIX/FLU showed a significantly better protective and curative potential than BIX.

Example 3

Characterization of the Curative Potential of Fluopyram, Bixafen and Fluxapyroxad in Controlling *Drechslera tritici-repentis* (DTR, Also Named *Pyrenophora tritici-Repentis*) Causing Tan Spot Materials and Methods
Crop: winter wheat (cv. Tommi (E06 2997))
Inoculation: *Drechslera tritici-repentis* (DTR, also named *Pyrenophora tritici-repentis*) spore suspension (0.14 Mio. Spores/ml) of DTR carried out 12 days after sowing
Fungicide application: 1, 4 & 8 days after inoculation, spray volume=250 L/ha, fungicide application in spraying cabinet
Replicates=six/treatment
Assessment of infected leaf area 21 days after inoculation (% efficacy calculated according to Abbott)

TABLE 10

| Treatment | | | | |
|---|---|---|---|---|
| Treatment | Active ingredients | Formulation | g a.i./ha | |
| 1 | UTC | — | — | — |
| 2 | Bixafen | 125EC | 125 | 97.5 |
| 3 | Fluopyram | 150EC | — | 97.5 |
| 4 | Fluxapyroxad | 62.5EC | 125 | 97.5 |
| 5 | Bixafen + Prothioconazole | 225EC | 97.5 + 195 | — |
| 6 | Bixafen + Fluopyram + Prothioconazole | 260EC | 97.5 + 97.5 + 195 | — |
| 7 | Fluxapyroxad + Epoxiconazole | 125EC | 125 + 125 | — |

TABLE 11

| Results | | | | |
|---|---|---|---|---|
| Active ingredients | Formulation | Amount in L/ha (g a.i./ha) | Efficacy [% Abbott] | |
| | | | 1 dai | 4 dai |
| Bixafen | 125EC | 0.78 (97.5) | 91 | 38 |
| Bixafen | 125EC | 1 (125) | 91 | 32 |

TABLE 11-continued

Results

| Active ingredients | Formulation | Amount in L/ha (g a.i./ha) | Efficacy [% Abbott] 1 dai | 4 dai |
|---|---|---|---|---|
| Fluopyram | 150EC | 0.65 (97.5) | 97 | 49 |
| Fluxapyroxad | 62.5EC | 1.56 (97.5) | 93 | 24 |
| Fluxapyroxad | 62.5EC | 2 (125) | 94 | 32 |
| Bixafen + Prothioconazole | 225EC | 1.3 | 97 | 38 |

Inoculation Schedula: 1 d(ay), 1 w(eek), 3 w, 4 w after application; Spray inoculation of a spore suspension of cryoconservated spores (conc. 1 Mio spores/mL; 1 bar pressure) nozzle type flat jet 1.3 mm Pathogen: Septoria tritici (Mycosphaerella graminicola)

Incubation: Incubation at 20° C. and 100% humidity in an incubation desk, no light for 2 days (=48 hours); another 2 days (48 hours) in a foil chamber at 15° C. and 100% humidity, 12 hours light, 12 hours darkness Cultivation: In a greenhouse chamber at 15° C. and 80% humidity;

TABLE 12

Assessment: 21 dai (days after inoculation); Assessment of plants inoculated 1 d, 1 w, 3 w, and 4 w after application

| Treatment | Active ingredients | Formulation | Amount [L/ha] | Efficacy [% Abbott] Inoculation after application | | | |
|---|---|---|---|---|---|---|---|
| | | | | 1 d | 1 w | 3 w | 4 w |
| 1 | UTC | UTC | | | | | |
| 2 | Bixafen + Prothioconazole | 225EC | 0.5 | 94.0 | 80.7 | 57.8 | 8.8 |
| 3 | Bixafen + Prothioconazole | 225EC | 1.0 | 95.5 | 84.3 | 60.0 | 26.3 |
| 4 | Isopyrazam + Epoxyconazole | 215SC | 0.4 | 91.0 | 81.9 | 31.1 | 10.5 |
| 5 | Isopyrazam + Epoxyconazole | 215SC | 0.8 | 91.0 | 86.7 | 60.0 | 26.3 |
| 6 | Fluxapyroxad + Epoxiconazole | 125EC | 0.8 | 94.0 | 81.9 | 72.2 | 17.5 |
| 7 | Fluxapyroxad + Epoxiconazole | 125EC | 1.6 | 92.5 | 86.7 | 70.0 | 42.1 |
| 8 | Bixafen + Fluopyram + Prothioconazole | 260EC | 0.75 | 91.0 | 85.5 | 74.4 | 53.5 |
| 9 | Bixafen + Fluopyram + Prothioconazole | 260EC | 1.5 | 92.5 | 89 | 73.3 | 57.9 |

TABLE 11-continued

Results

| Active ingredients | Formulation | Amount in L/ha (g a.i./ha) | Efficacy [% Abbott] 1 dai | 4 dai |
|---|---|---|---|---|
| Bixafen + Fluopyram + Prothioconazole | 260EC | 1.5 | 95 | 73 |
| Fluxapyroxad + Epoxiconazole | 125EC | 2.0 | 93 | 27 |

Bixafen + Prothioconazole + Fluopyram at 1.5 L/ha demonstrates a better curative activity than Bixafen + Prothioconazole and Fluxapyroxad + Epoxiconazole.

Example 4

Characterization of the Preventive Potential of Active Compound Combinations of the Present Invention in Controlling Septoria tritici (Mycosphaerella graminicola) in Wheat Materials and Methods Seed: Wheat "Monopol", Substrate: Peat Soil, Type "T", Pot: 7×7×7 cm, 10-15 seeds/pot Application: Spray-application at the Slide spraying cabine with 250 l/ha Application date: BBCH 12-13

Replicates/Treatment: 5 pots

The results show that Bixafen+Fluopyram+Prothioconazole demonstrated significantly improved long term preventive (protective) effect against Septoria tritici (Mycosphaerella graminicola) in wheat as compared to Bixafen+Prothioconazole, Isopyrazam+Epoxyconazole, and Fluxapyroxad+Epoxiconazole.

The invention claimed is:

1. An active compound combination comprising
   (A) fluopyram and
   (B) bixafen and
   (C) at least one triazole fungicide, which is prothioconazole,
   wherein (A), (B), and (C) are the sole fungicides in the combination and wherein the weight ratios of A:B and B:C and A:C are independently each 25:1 to 1:25.

2. Composition comprising active compound combination according to claim 1 and further comprising one or more of auxiliaries, solvents, carriers, surfactants and/or extenders.

3. Method for improving growth in one or more crops, comprising applying an active compound combination according to claim 1 to seed, a plant, to fruit of a plant and/or to soil on which the plant grows or is supposed to grow, each including seed of a transgenic plant and/or a transgenic plant.

4. Method according to claim 3, wherein improved growth comprises at least one selected from the group consisting of preventively and/or curatively controlling pathogenic fungi and/or nematodes, resistance management, and improved plant physiology effects selected from enhanced root growth, improved greening, improved water use efficiency, improved nitrogen-use efficiency, delayed senescence and enhanced yield.

5. Method according to claim 3, wherein improved growth comprises at least one selected from the group consisting of better growth, increased harvest yields, a better developed root system, a larger leaf area, greener leaves and stronger shoots.

6. Method for improving growth in one or more crops comprising preventively and/or curatively controlling pathogenic fungi and/or nematodes,
comprising applying an active compound combination comprising
(A) fluopyram and
(B) bixafen and
(C) at least one triazole fungicide
to seed, a plant, to fruit of a plant and/or to soil on which the plant grows or is supposed to grow, each including seed of a transgenic plant and/or a transgenic plan
wherein preventive control of pathogenic fungi and/or nematodes is still observed when the seed or the plant is infested with pathogenic fungi and/or nematodes up to four weeks after application of the active compound combination.

7. Method according to claim 3, wherein in treatment of leaves, from 0.1 to 10 000 g active compound combination/ha and in treatment of seed, from 2 to 200 g active compound combination per 100 kg of seed are employed.

8. A fungicidal composition comprising
(A) fluopyram and
(B) at least one further succinate dehydrogenase (SDH) inhibitor comprising biaxafen and further
(C) at least one triazole fungicide comprising prothioconazole
wherein the composition improves growth in one or more crops, wherein improvement comprises at least one selected from the group consisting of preventively and/or curatively controlling pathogenic fungi and/or nematodes, resistance management, and improved plant physiology effects selected from enhanced root growth, improved greening, improved water use efficiency, improved nitrogen-use efficiency, delayed senescence and enhanced yield.

9. A method according to claim 4, wherein resistance management is improved and is defined as prevention and/or delay of development of insensitivity of pathogenic fungi to the fungicidal composition.

10. A method according to claim 4, wherein pathogenic fungi are controlled which are selected from the group consisting of *Tapesia/Oculimacula /Pseudocercosporella* species, *Septoria tritici, Leptosphaeria nodorum, Puccinia triticiana, Puccinia striiformis, Pyrenophora/Drechslera tritici-repentis, Blumeria graminis/Erysiphe graminis, Fusarium* spp., *Rhynchosporium secalis, Pyrenophora/Drechslera teres, Puccinia hordei*, and *Ramularia collocygni*.

11. A method according to claim 3 comprising treatment of cereals selected from the group consisting of wheat and barley.

12. A method according to claim 6, wherein the at least one triazole fungicide comprises prothioconazole.

13. A combination according to claim 1, wherein compounds (A), (B), and (C) are present in a synergistically effective amounts and are the sole active compounds in the combination.

14. A combination according to claim 1, wherein the weight ratios of A:B and B:C and A:C are independently each 10:1 to 1:10.

15. A combination according to claim 1, wherein the weight ratios of A:B and B:C and A:C are independently each 5:1 to 1:5.

16. A combination according to claim 1, wherein the weight ratio of A:B:C is 1:0.5:1 to 1:1.5:3.

17. A combination according to claim 1, wherein the weight ratio of A:B:C is 1::1 to 2.

18. A method according to claim 12, wherein the weight ratios of A:B and B:C and A:C are independently each 10:1 to 1:10.

19. A method according to claim 12, wherein the weight ratios of A:B and B:C and A:C are independently each 5:1 to 1:5.

* * * * *